United States Patent
Spolin et al.

(10) Patent No.: US 9,277,870 B2
(45) Date of Patent: Mar. 8, 2016

(54) INFANT MONITORING SYSTEM AND METHODS

(71) Applicant: Sproutling, Inc., San Francisco, CA (US)

(72) Inventors: Mathew Spolin, San Francisco, CA (US); Christopher Bruce, San Francisco, CA (US)

(73) Assignee: Sproutling, Inc., San Francisco, CA (US)

( * ) Notice: Subject to any disclaimer, the term of this patent is extended or adjusted under 35 U.S.C. 154(b) by 0 days.

(21) Appl. No.: 14/485,396

(22) Filed: Sep. 12, 2014

(65) Prior Publication Data

US 2015/0094544 A1    Apr. 2, 2015

Related U.S. Application Data

(60) Provisional application No. 61/877,067, filed on Sep. 12, 2013.

(51) Int. Cl.
*A61B 5/00* (2006.01)
*G06F 19/00* (2011.01)
(Continued)

(52) U.S. Cl.
CPC ........... *A61B 5/02444* (2013.01); *A61B 5/0008* (2013.01); *A61B 5/01* (2013.01); *A61B 5/0205* (2013.01); *A61B 5/02055* (2013.01); *A61B 5/02438* (2013.01); *A61B 5/11* (2013.01); *A61B 5/4809* (2013.01); *A61B 5/6831* (2013.01); *A61B 5/7275* (2013.01); *A61B 5/746* (2013.01);
(Continued)

(58) Field of Classification Search
CPC .. A61B 5/4809; A61B 5/4812; A61B 5/4815; A61B 5/0205; A61B 5/72; A61B 5/7264; A61B 5/0002; A61B 2503/04; A61B 2503/045; G06F 19/3418; G06F 19/3437; G06F 19/345
See application file for complete search history.

(56) References Cited

U.S. PATENT DOCUMENTS 6,553,242 B1    4/2003 Sarussi
6,743,167 B2 *  6/2004 Balkin et al. .................. 600/137
(Continued)

FOREIGN PATENT DOCUMENTS

WO    WO 2013093686 A1 *  6/2013

OTHER PUBLICATIONS

Borbely, A. A. et al; "Concepts and models of sleep regulation: an overview"; J. Sleep Res. (1992) 1, 63-19.*
(Continued)

*Primary Examiner* — William Thomson
*Assistant Examiner* — Marie Archer
(74) *Attorney, Agent, or Firm* — Jeffrey Schox; Ivan Wong

(57) ABSTRACT

One variation of a method for monitoring sleep of a user includes: assigning a collective wakefulness model—generated from sleep data collected from a set of other users—to the user for a first time period; storing a first set of vitals data collected by a wearable device worn by the user during first time period; extrapolating, from the collective wakefulness model, a first waking time of the user for a first sleep event during first time period based on data in the first set of vitals data; queuing the first waking time for transmission to a mobile computing device linked to the account for presentation to a guardian of the user; in response to expiration of the first time period, generating an individual wakefulness model specific to the user based on the first set of vitals data collected during the first time period.

11 Claims, 8 Drawing Sheets

(51) Int. Cl.
| | |
|---|---|
| A61B 5/024 | (2006.01) |
| A61B 5/0205 | (2006.01) |
| A61B 5/11 | (2006.01) |
| A61B 5/01 | (2006.01) |
| G06F 1/32 | (2006.01) |

(52) U.S. Cl.
CPC ............ *G06F 1/3206* (2013.01); *G06F 19/345* (2013.01); *G06F 19/3418* (2013.01); *G06F 19/3437* (2013.01); *A61B 5/0022* (2013.01); *A61B 5/024* (2013.01); *A61B 5/6829* (2013.01); *A61B 2503/04* (2013.01); *A61B 2560/0209* (2013.01); *A61B 2560/0242* (2013.01); *A61B 2562/00* (2013.01)

(56) References Cited

U.S. PATENT DOCUMENTS

| | | | |
|---|---|---|---|
| 7,006,855 B1 | 2/2006 | Sarussi | |
| 7,171,251 B2 | 1/2007 | Sarussi et al. | |
| 7,359,741 B2 | 4/2008 | Sarussi | |
| 7,590,438 B2 | 9/2009 | Sarussi et al. | |
| 7,603,152 B2 | 10/2009 | Sarussi et al. | |
| 7,606,607 B2 | 10/2009 | Sarussi et al. | |
| 7,613,490 B2 | 11/2009 | Sarussi et al. | |
| 7,650,176 B2 | 1/2010 | Sarussi et al. | |
| 7,898,426 B2 * | 3/2011 | Rai et al. | 340/575 |
| 8,484,153 B2 * | 7/2013 | Mott et al. | 706/52 |
| 2005/0080349 A1 * | 4/2005 | Okada et al. | 600/534 |
| 2006/0293608 A1 * | 12/2006 | Rothman et al. | 600/545 |
| 2007/0156060 A1 * | 7/2007 | Cervantes | 600/534 |
| 2008/0157956 A1 * | 7/2008 | Radivojevic et al. | 340/531 |
| 2010/0271469 A1 * | 10/2010 | She | 348/77 |
| 2010/0331630 A1 * | 12/2010 | Odio | 600/301 |
| 2011/0034811 A1 * | 2/2011 | Naujokat et al. | 600/484 |
| 2011/0190594 A1 * | 8/2011 | Heit et al. | 600/301 |
| 2011/0261182 A1 * | 10/2011 | Lee et al. | 348/77 |
| 2011/0301487 A1 * | 12/2011 | Abeyratne et al. | 600/544 |
| 2013/0218035 A1 * | 8/2013 | Masuda | 600/508 |
| 2014/0297600 A1 * | 10/2014 | Kan et al. | 707/688 |
| 2015/0119741 A1 * | 4/2015 | Zigel et al. | 600/529 |

OTHER PUBLICATIONS

Borbely, A. A. et al; "Sleep Homeostasis and Models of Sleep Regulation"; Journal of Biological Rythms, vol. 14 No. 6, Dec. 1999; 559-568.*

Bowe, T. R. et al; "The use of the Semi-Markov model in the study of the Development of Sleep-Wake States in Infants"; Psychophysiology; vol. 16; No. 1, 1979, p. 41-48.*

Burnham, M. M. et al; "Nighttime sleep-wake patterns and self-soothing from birth to one year of age: a longitudinal intervention study"; J Child Psychol Psychiatry. Sep. 2002; 43(6): 713-725.*

Elias, M. F. et al. "Sleep/wake patterns of Breast-Fed Infants in the First 2 years of life"; Pediatrics, vol. 77; No. 3, Mar. 1986; p. 322-329.*

Halpern, L. F. et al; "Infant Sleep-Wake Characteristics: Relation to Neurological Status and the Prediction of Developmental Outcome"; Developmental Review 15, 255-291 (1995).*

Galland, B. C. et al; "Normal sleep patterns in infants and children: A systematic review of observational studies"; Sleep Medicine Reviews 16 (2012) 213-222.*

Jenni, O. G.; "Understanding sleep-wake behavior and sleep disorders in children: the value of a model"; Curr Opin Psychiatry. May 2006; 19(3): 282-287.*

Blampied, N. M. et al; "A Behavioral Model of Infant Sleep Disturbance"; Journal of Applied Behavior Analysis; 1993; 26, 477-492.*

Pollack, C. P.; "Regulation of Sleep Rate and Circadian Consolidation of Sleep and Wakefulness in an Infant"; Sleep; 17 (7):567-575; 1994.*

* cited by examiner

INFANT MONITORING SYSTEM AND METHODS

CROSS-REFERENCE TO RELATED APPLICATIONS

This application claims the benefit of U.S. Provisional Application No. 61/877,067, filed on 12 Sep. 2013, which is incorporated in its entirety by this reference.

TECHNICAL FIELD

This invention relates generally to the field of wearable devices and more specifically to a new and useful system and methods for monitoring an infant in the field of wearable devices.

DESCRIPTION OF THE EMBODIMENTS

The following description of the embodiments of the invention is not intended to limit the invention to these embodiments, but rather to enable any person skilled in the art to make and use this invention.

1. System

Figure 1:
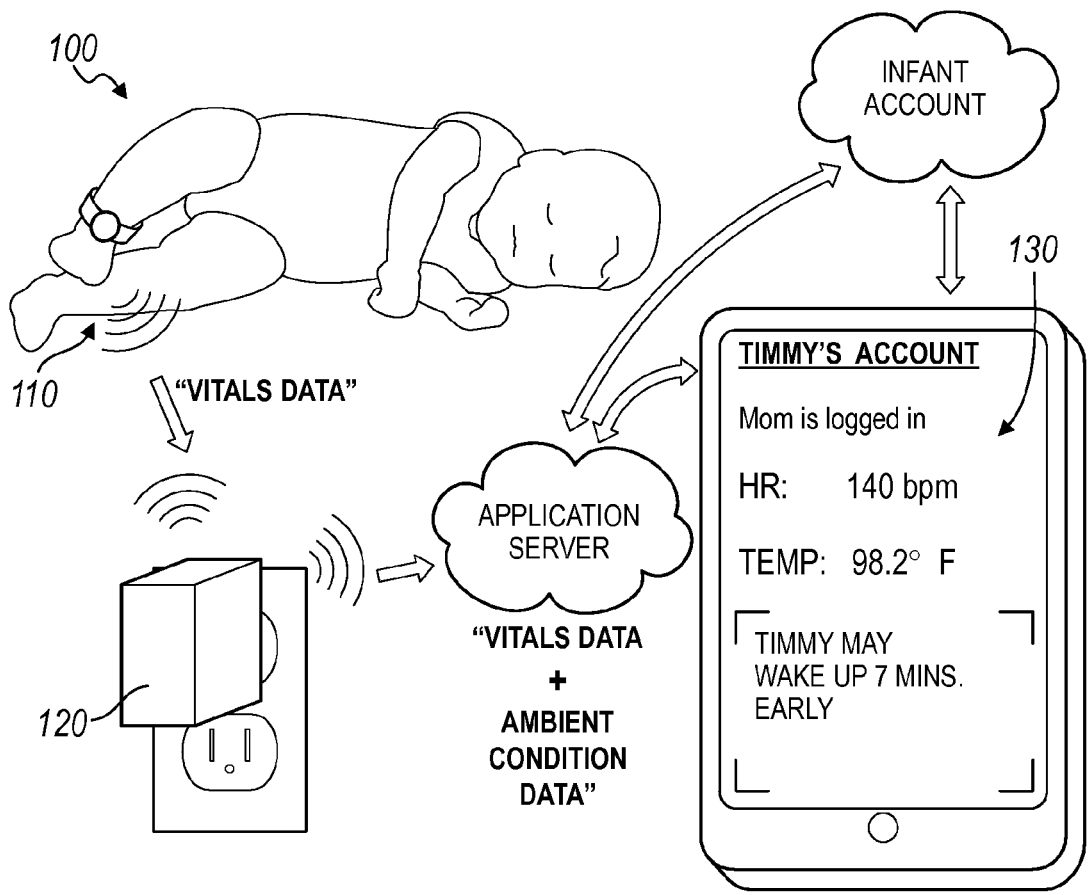
FIG. 1 is a flowchart representation of a system in accordance with the invention.

As shown in FIG. 1, a system for monitoring an infant includes: a wearable device no including a heart rate sensor, a skin temperature sensor, and a wireless transmitter; a base station 120 including an ambient temperature sensor, an ambient light sensor, and a wireless receiver; an application server 140 transforming infant vitals data received from the wearable device and ambient data received from the base station into predicted wake time of the infant from a sleep event; and a user interface 130 accessible through a computing device and presenting the predicted wake time of the infant and infant-related alerts substantially in real time.

2. Applications

Generally, the system functions: to collect vitals data of an infant (i.e., the "user") through a wearable device worn by the infant and to collect ambient condition data of a space occupied by (or proximal) the infant through a base station and/or through a local mobile computing device over time, to generate a wakefulness (e.g., sleep-related) model of the infant based on the vitals and ambient condition data, to extrapolate (i.e., predict) an upcoming infant-related event based on the wakefulness model and current infant vitals and ambient condition data, and to push alerts and notifications for the upcoming infant-related event to a parent or guardian of the infant —through a related computing device—substantially in real-time. In particular, the system incorporates various hardware and software elements that cooperate to implement various methods and techniques: to collect infant vitals and ambient data over time; to model a physiological state (e.g., wakefulness) of the infant—such as for a particular development stage of the infant—based on these data; to make projections of future events related to the physiological state of the infant (e.g., a particular time that the infant will wake from a nap); and to preemptively present these projections to a guardian (e.g., a parent, a grandparent, a babysitter, etc.) of the infant through a smartphone, tablet, smartwatch, or other computing device associated with the guardian. In one example, the system tracks vital signs (e.g., heart rate, skin temperature) of the infant and ambient conditions near the infant during the infant's napping periods, systematically processes a wakefulness model assigned to or generated specifically for the infant based on these infant vitals and the ambient conditions data to extrapolate and revise a predicted time that the infant will wake from the napping period, and systematically updates a visual interface rendered on a parent's mobile computing device (e.g., smartphone, tablet) according to the extrapolated and revised predicted times that the infant will wake from the nap.

The system includes an application server that stores infant and infant-relevant ambient data with an account assigned to the infant. The system includes a wearable device incorporating various sensors that measure various infant vitals, such as heart rate and skin temperature, and a wireless transmitter that uploads these vitals to the infant's account (e.g., within a remote database linked to the application server), such as through a base station or through an external computing device (e.g., a parent's smartphone or tablet) affiliated with the infant's account. The system also includes a base station incorporating various sensors that detect ambient conditions, such as temperature, humidity, light level, and noise level, and a wireless transmitter that uploads these ambient conditions data to the infant's account, such as through a local Wi-Fi router. The application server can apply these vitals and ambient condition data to a current physiological state model assigned to the infant to output predictions for changes to the infant's physiological state, such as a particular time that the infant will wake from a nap. The application server can also store these vitals and ambient condition data over time and can generate new physiological state models (or retrain existing infant-specific physiological state models) specific to the infant over time as new infant-related data is collected. Alternatively, the base station and/or the native application executing on a computing device linked to the base station and/or to the infant's account can execute these methods and techniques.

The system can further generate a collective physiological (e.g., wakefulness) model generic to a population of infants based on data collected from infants in this population of infants over time and then apply this collective physiological model to the (particular) infant to predict future physiological state changes for the infant. For example, the system can assign a collective physiological model to the infant if sufficient data specific to the infant is not currently available or extant, such as when the infant's account is first activated, to enable rough predictions of future physiological state changes of the infant to be made during a first use of the system. In this example, once sufficient data is collected from the infant, such as after a first week of use of the system, the system can generate a new collective physiological model specific to the infant based on these data collected from the infant and the infant's surrounding, such as to the exclusion of data collected from other infants in the infant population.

Elements of the system can be implemented on one or more computer networks, computer systems, or applications servers, etc. The computer system(s) can be a cloud-based computer, a mainframe computer system, a grid-computer system, or any other suitable computer system, and the computer system can support collection of data from a wearable device and/or a base station, processing of these data, and transmission of alerts, notifications, and/or user interface updates to one or more (mobile) computing devices linked to or affiliated with the infant's account. For example, the computer system can receive infant vitals data and distribute alerts and notifications over a distributed network, such as over a cellular network or over an Internet connection. In this example, the computer system can upload alerts and notifications to a native infant monitoring application including the user interface and executing on a guardian's mobile computing device.

Additionally or alternatively, a mobile computing device associated with the system (e.g., with the infant's account)—such as a laptop computer, a desktop computer, a tablet, a smartphone, a personal data assistant (PDA), etc. —can maintain the infant's account, create and maintain an infant-specific physiological model within the account, and execute a native infant monitoring application (including the user interface) to generate, receive, and/or display alerts and notifications and/or update physiological state change predictions for presentation to a corresponding parent or guardian.

3. Wearable Device

Figure 2:
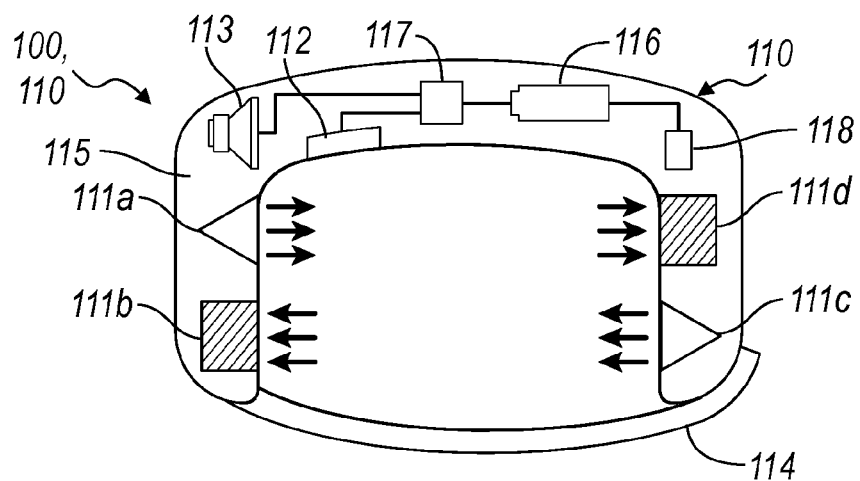
FIG. 2 is a schematic representation of one variation of the system.

As shown in FIG. 2, the wearable device of the system includes a heart rate sensor 111, a skin temperature sensor 112, and a wireless transmitter 113. Generally, the wearable device functions to collect various vitals data from the infant and to transmit these vitals data to an external device, such as to the base station or to a local mobile computing device wireless paired to the base station and/or to the wearable device.

The wearable device can include a band 114, such as a food-safe or skin-safe (e.g., silicone) band containing or supporting a housing 115 containing the foregoing sensors, the wireless transmitter (or transceiver, wireless communication module), and a battery 116, etc. in a dust-resistant, dust-proof, water-resistant, and/or water-proof cavity. The band can be of an adjustable size to enable application of the wearable device onto infants of different sizes and/or the same infant as the infant grows over time. The band can be configured to retain one or more of the foregoing sensors (e.g., the skin temperature sensor, the heart rate sensor) adjacent the infant's skin to enable substantially accurate detection of corresponding vital signs. The band can be configured to engage (e.g., rest on, couple to) an infant's ankle, wrist, waist, chest, toe, or other suitable portion of the infant's body.

The wearable device can also include a processor 117 configured to locally compress, analyze, filter, timestamp, or otherwise manipulate data collected through sensors integrated into the wearable device before these sensor data are offloaded from the wearable device, such as to the base station and/or to a local computing device.

In one implementation of the wearable device, the heart rate sensor includes an optical emitter 111A and an optical detector 111B that cooperate to optically detect heart pulses of the infant on which the wearable device is installed. For example, the heart rate sensor can include a first optical (e.g., infrared, or "IR") emitter 111A and a first optical detector 111B paired with and adjacent the first optical emitter, wherein the first optical emitter outputs light in the IR spectrum and the first optical detector outputs a signal corresponding to detected IR light originating from the first optical emitter and reflected from the infant's skin back into the first optical detector. In this example, a processor within the wearable device correlates a change in the signal output from the first optical emitter with a heart pulse, identifies a series of heart pulses over a period of time (e.g., three seconds) and calculates the infant's heart rate based on the number of pulses detected over the period of time.

As shown in FIG. 2, in the foregoing implementation, the heart rate sensor can also include a second optical emitter 111C and a second optical detector 111D paired with and adjacent the second optical emitter, and the second optical emitter can output light in the IR spectrum and the second optical detector can output a signal corresponding to detected IR originating from the second optical emitter and reflected from the infant's skin back into the second optical detector. In this implementation, the band of the wearable device can define a loop, and the second optical emitter and the second optical detector can be arranged on the loop opposite the first optical emitter and the first optical detector. Alternatively, the first optical emitter/detector pair can be arranged near one end of the housing (supported by the band), and the second optical emitter/detector pair can be arranged near the opposite end of the housing. The processor—also arranged within the band or within the housing—can calculate the infant's heart rate based on a frequency of oscillating signals output from the second optical emitter if sensor data from the first optical detector gives false, improbable, or unlikely results, such as if the processor calculates a heart rate of less than twenty beats per minute ("bpm") or greater than 200 bpm. The second optical emitter/detector pair can thus function as a redundant sensor system, and the processor can detect and confirm failure of the first optical emitter/detector pair based on outputs of the second optical emitter/detector pair.

The processor can additionally or alternatively calculate a first infant heart rate based on signals from the first optical detector and a second infant heart rate based on signals from the second optical detector substantially simultaneously and then compare the first and second calculated heart rates to confirm the first calculated heart rate. If the first and second calculated heart rates are substantially similar (e.g., within 5 bpms, or within ±3%), the processor can average the first and second heart rates. However, if the first and second calculated heart rate differ significantly (e.g., by more than one of the foregoing relative amounts), the processor can trigger the first optical emitter to output an IR signal, the second optical detector can output a third signal based on detected IR light originating from the first optical emitter and transmitted through the infant's skin, and the processor can calculate a third infant heart rate from the third signal, compare the first and second heart rates to the third heart rate, and eliminate an incorrect heart rate calculation—from the three heart rate calculations—based on similarities between the two of the three heart rate calculations. The processor can then average the two remaining heart rate calculations to estimate a current infant heart rate. However, the heart rate sensor can include any other type of heart rate sensor, and the processor arranged within the wearable device can handle data received from the heart rate sensor(s) to implement sensor redundancy and to calculate a heart rate of the infant in any other suitable way.

The wearable device can also include a skin temperature sensor 112, such as an infrared thermometer, a resistance thermometer, a silicon bandgap temperature sensor, or a thermistor. For example, the skin temperature sensor can include an infrared thermometer arranged across an inner (i.e., skinfacing) surface of the housing and adjacent the heart rate sensor, and the processor can sample an output of the infrared thermometer during periods when the optical emitter of the heart rate sensor is not outputting IR light. The band of the wearable device can thus retain the housing against a portion of the infant's body such that the skin temperature sensor and the heart rate sensor face the infant's skin to enable detection of the infant's skin temperature and heart rate, respectively.

The wearable device can further include an ambient temperature sensor, such as arranged across on outer surface of the housing opposite the skin temperature sensor. In one example implementation, the processor transitions the wearable device from a low-power mode (e.g., a sleep or hibernate state, a wireless-disabled state) into a test mode or into an active mode (e.g., an 'ON' state, a wireless-enabled state) when an output of the skin temperature sensor and an output of the ambient temperature sensor indicate a temperature gradient—across the housing—that exceeds a threshold temperature, such as 10° F. In this example, while the wearable device is in the low-power, the processor can sample the skin temperature sensor and the ambient temperature sensor at a relatively low sampling rate (e.g., 1 Hz), compare outputs of the skin temperature sensor and the ambient temperature sensor, and —in response to the difference between the detected skin temperature and the detected ambient temperature that exceeds a preset threshold—transitions the wearable device into the test mode or into the active mode in which the processor samples the heart rate sensor and the skin temperature sensor at a higher rate (e.g., 10 Hz) and wirelessly transmits heart rate and skin temperature data, such as to the base station or to a local mobile computing device, as described below.

Alternatively, the processor can track changes in outputs of the skin temperature sensor over time, such as while the wearable device is in the test mode, and the processor can transition the wearable device from the low-power mode into the active mode when detected skin temperatures increase by at least threshold temperature within at least a threshold period of time, such as least 5° F. within a five-second interval, which indicates that the wearable device was recently installed onto the infant, as described below. Once in the active mode, the processor can then sample the heart rate sensor to collect heart rate data, sample an accelerometer or other motion sensor within the wearable device to collect motion data, sample a position sensor within the wearable device to collect orientation data, etc. and then interface with the wireless transmitted within the wearable device to communicate these data to the base station or to an other paired mobile computing device as described below.

Additionally or alternatively, the processor can automatically transition the wearable device from the low-power mode into the active mode based on one or more of motion (e.g., acceleration, orientation) data, heart rate data, and/or other data collected locally at the wearable device. For example, while in the low-power mode, the processor can occasionally (e.g., at a rate of 1 Hz) trigger the first optical emitter of the heart rate sensor and sample a corresponding output signal from the second optical detector of the hear rate sensor (which substantially faces the first optical emitter) to determine if the annulus of the band of the wearable device is obstructed, such as by the infant's ankle; if the annulus is obstructed, the processor can transition from the low-power mode into the test mode. Once in the test mode, the processor can: sample a motion sensor (e.g., an accelerometer) arranged within the wearable device to determine if a cyclic change in position, velocity, or acceleration output from the motion sensor substantially aligns with a modeled (infant) breathing pattern; sample the skin temperature sensor to determine if a current skin temperature sensor output falls within a known human skin temperature range; and transition the wearable device into the active mode accordingly.

The wearable device can also include a motion sensor 118—such as a tilt sensor, an accelerometer, and/or a gyroscope—that outputs a signal corresponding to an orientation or a change in orientation of the wearable device. The wearable device can also include a proximity sensor—such as a capacitive proximity sensor arranged across an inner face of the housing or an optical proximity sensor (physically coextensive with the heart rate sensor)—that outputs a signal corresponding to proximity of a surface to the wearable device. In one example implementation, as described below, the wearable device includes a tilt sensor electrically coupled to an interrupt pin of the processor, and the processor transitions from the low-power mode (e.g., a hibernate setting) into a test mode in response to receipt of a signal from the tilt sensor. Once in the test mode, the processor samples the proximity sensor to detect a surface of an external object proximal the inner surface of the housing. If no external object is detected, the processor can transition the wearable device back into the low-power mode. However, if a surface if detected adjacent the wearable device, the processor then samples the skin temperature sensor to determine that the detected external object adjacent the wearable device is human, such as if a sequence of outputs of the skin temperature sensor indicate an increase in temperature over a short period of time (e.g., 2° F. increase within a one-second interval) commensurate with installation of the wearable device over a limb of living human or if a temperature output from the skin temperature sensor indicates that the temperature of the surface of the external object falls within an expected range of human skin temperatures (e.g., 98° F.±8° F.). The processor can then transition from the test mode directly into the active mode based on an output from the skin temperature sensor that indicates that the external surface is human. However, if the skin temperature sensor returns a temperature or a temperature change outside of values expected for an adjacent surface that is human, the processor can transition the wearable device back into the low-power mode. Alternatively, the processor can remain in the test mode and sample the heart rate sensor in response to an output from the skin temperature sensor that indicates that the detected adjacent external surface is human. If the heart rate sensor outputs an oscillating signal indicative of a heartbeat (e.g., a signal oscillating at a frequency within a typical range of a human infant), the processor can transition the wearable device into the active mode. However, if a signal output from the heart rate sensor does not substantially align with a heart beat of a human infant, the processor can transition the wearable device back into the low-power mode.

Once in the active mode, the processor can sample the heart rate sensor, the skin temperature sensor, the motion sensor, and/or any other sensor arranged within the wearable device, and the wireless transmitter within the wearable device can transmit data collected from these sensors to a paired base station and/or to a paired mobile computing device, such as in raw, filtered, or compressed forms. For example, while in the active mode, the processor can sample an accelerometer (or other motion sensor arranged) within the wearable device, filter noise out of motion data received from the accelerometer, and characterize these motion data by matching these segments of these motion data to motion type models. In this example, the processor can characterize a series of acceleration data with one of steady breathing, coughing, sneezing, crying, writhing, rolling, and/or crawling based on corresponding motion models stored locally on the wearable device. The processor can then pass a code for a characterized motion and a duration of the characterize motion to the wireless transmitter for broadcast to the base station and/or external mobile computing device.

In another example, once in the active mode, the processor can sample an orientation sensor arranged within the wearable device, determine that the infant wearing the wearable device is inverted (i.e., on its stomach) if based on an output of the orientation sensor, and pass an alarm to the wireless transmitter for broadcast to the base station and/or external mobile computing device. In this example, the wearable device can be configured for installation in a single orientation over an extremity of an infant (e.g., an ankle) or define a geometry suggesting a preferred orientation of the wearable device on an infant, and the processor can compare an output of the orientation sensor to a known "upright" orientation of the wearable device (based on the preferred orientation of the wearable device) to determine if the infant has rolled over. Alternatively, the processor can sample the orientation sensor substantially soon after entering the active mode and store this orientation as the "upright" orientation, the processor can compare subsequent outputs of the orientation sensor to the "upright" orientation to determine if the infant has rolled over. In this example, the processor can pass an alarm to the wireless transmitter for broadcast to the base station, etc. if a detected orientation of the wearable device falls outside of an acceptable range of the "upright" orientation for a threshold duration, such as if the detected rotational orientation of the wearable device shifts by more than 80° from the "upright" orientation about a central axis of the annulus of the band attaching the wearable device to the extremity of the infant. However, the wearable device can include any other type of motion sensor and/or orientation sensor, and the processor can process data from this/these sensors in any other suitable way.

The processor can also sample the skin temperature sensor, the heart rate sensor, and/or the proximity sensor, etc. to determine if the wearable device has been removed from the infant, and the processor can transition the wearable device back into the low-power mode or the test mode accordingly. For example, if the skin temperature sensor detects a sudden drop in temperature (e.g., 5° F. within one second) and the heart rate sensor no longer senses a heart rate, the processor can determine that the wearable device has been removed from the infant even if the proximity sensor indicates that the wearable device is still adjacent a surface; the processor can thus transition the wearable device back into the low-power mode. However, in this example, if the proximity sensor does not indicate that the wearable device has been removed from an adjacent surface and the skin temperature sensor does not indicate that a significant change in the skin temperature of the adjacent surface but the heart rate sensor detects a shift in heart rate outside of a normal heart rate range, the processor can trigger the wireless transmitter to broadcast a corresponding alarm to the base station or mobile computing device wirelessly paired to the wearable device. Similarly, if the proximity sensor does not indicate that the wearable device has been removed from an adjacent surface and the heart rate sensor detects a heart rate within a normal heart rate range but the skin temperature sensor detects a skin temperature outside of a normal temperature range, the processor can trigger the wireless transmitter to broadcast a corresponding alarm to the base station and/or to the mobile computing device. However, the processor can manipulate data received from various sensors within the wearable device to transition the wearable device back into the low-power mode or into the test mode and to trigger the wireless transmitter to transmit an alarm to the base station or a local mobile computing device.

The wearable device therefore also includes a wireless communication module. In one implementation, the wireless communication module includes a wireless transmitter, such as a Bluetooth transmitter or other radio-frequency-based wireless transmitter. The wireless transmitter can upload data collected through various sensors arranged within the wearable device (e.g., heart rate data, motion data, skin temperature data, etc.) to the base station and/or to a mobile computing device, such as substantially in real-time as data is collected at the wearable device or asynchronously, such as every thirty seconds, every five minutes, or every hour while the wearable device is in the active mode.

The processor can also prioritize various data transmitted from the wearable device. For example, the processor can select an abnormal heart rate or temperature readings (e.g., a heart rate of 35 bpm, a temperature of 102° F., or light or labored breathing) for immediate transmission by the wireless transmitter to the base station. In this example, the processor can set a low upload priority to normal motion characterizations (e.g., sneezing, crying, writhing) such that wireless transmitter uploads these motion characterizations to the base station one two-minute intervals. The processor can also store higher-density data (e.g., raw accelerometer data) locally on the wearable device and can trigger the wireless transmitter to upload these higher-density data to the base station or to a local mobile computing device on longer intervals (e.g., two hours) or after detected events, such as after the wearable device is removed from the infant and before the wearable device transitions back into the low-power mode or while the wearable device is recharging (as described below). Alternatively, the wireless transmitter can transmit collected sensor data to the base station and/or mobile computing device substantially in real-time (i.e., as data is collected and/or meaning information extrapolated therefrom).

The wireless module can also include a wireless receiver (or transceiver) that downloads data from the base station and/or from a mobile computing device wirelessly paired to the wearable device. In one example, the wireless receiver cooperates with the processor to download and install a software update received from the base station. In another example, the wireless receiver downloads an updated infant-specific model defining triggers and thresholds for prioritizing transmission of heart rate, motion, and/or temperature data to the base station, etc. In yet another example, the wireless receiver downloads new motion characterization models and motion definitions—such as such specific to the infant—to enable improved characterization of local motion data by the processor.

The wireless communication module can store (or access from another component within the wearable device) a unique identifier ('ID') assigned to the wearable device (or to the wireless communication module) and broadcast this unique identifier when establishing a wireless connection with the base station, with a local mobile computing device, or with any other local computing device. For example, the wireless communication module can transmit data collected by the wearable device with the unique ID assigned to the wearable device, and the base station or an application server affiliated with the system can store such that these data in an account or profile specific to the corresponding infant based on the unique ID. The wireless receiver within the wireless communication module can also receive an access key from the base station and/or from a local mobile computing device to confirm transmission of infant vitals data from the wearable device. For example, the wireless communication module can transmit its assigned unique ID to the base station, the base station can upload the wearable device unique ID and a unique ID assigned to the base station to an affiliated application server, which accesses an internal database, a registry of device identifiers, a domain name system ('DNS'), or other database to determine that the wearable device and base station IDs linked to a particular infant; the applications server then identifies a particular infant's account affiliated with the wearable device and/or with the base station and uploads a corresponding access key to the base station; the wireless receiver then receives the access key from the base station, and the wireless communication module or the processor confirms data transmission to the base station based on the access key before the wireless transmitter broadcasts infant vitals data collected on the wearable device back to the base station. The wearable device, the base station, a local mobile computing device, and/or the application server can implement similar methods or techniques to confirm communications between the wearable device and the local mobile computing device.

However, the wireless module can include any other suitable wireless receiver, transmitter, or transceiver supporting communication of data between the wearable device and the base station and/or one or more local mobile computing devices.

The processor can also maintain an internal clock or other timer and can store any of the foregoing sensor data or sensor-related data (e.g., calculated heart rate, motion characterization, detected skin temperature, etc.) with one or more timestamps indicating a time of and/or a time duration of each sensor data. As described below, the wearable device can also 'sync' with the base station and/or with the mobile computing device to update the internal clock with a real current time, such as if the internal clock drifted out of synchronicity with real time.

The wearable device can further include a battery 116 or other power supply to power the processor, the wireless transmitter, and/or various sensors within the wearable device. The battery can be a rechargeable battery, such as a rechargeable lithium-ion or lithium-polymer battery. For example, the wearable device can include a pair of metallic contacts passing through the housing and coupled to terminals of the battery such that the wearable device can be placed on a charging station and the battery thus recharged via the metallic contacts. Alternatively, the wearable device can include a wireless charging circuit arranged within the housing, the wireless charging circuit can recharge the battery when the wearable device is placed on a wireless charging station, such as a wireless charging station integrated into the base station. However, the battery can be any other suitable type of battery and can be recharged in any other suitable way.

4. Wearable Device: Modes

The wearable device can operate in various modes over time, such as a low-power mode in which various local processes and functions of the wearable device are discontinued, a test mode in which various sensors within the wearable device are sampled to automatically determine if the wearable device has been installed on an infant (i.e., a "user"), and an active mode in which the wearable device is actively collecting data through one or more internal sensors and is transmitting these data to an external device (e.g., the base station, a mobile computing device). As described above, the wearable device can automatically transition between the low-power, test, and active modes, such as based on sensor data collected locally on the wearable device.

Figure 6:
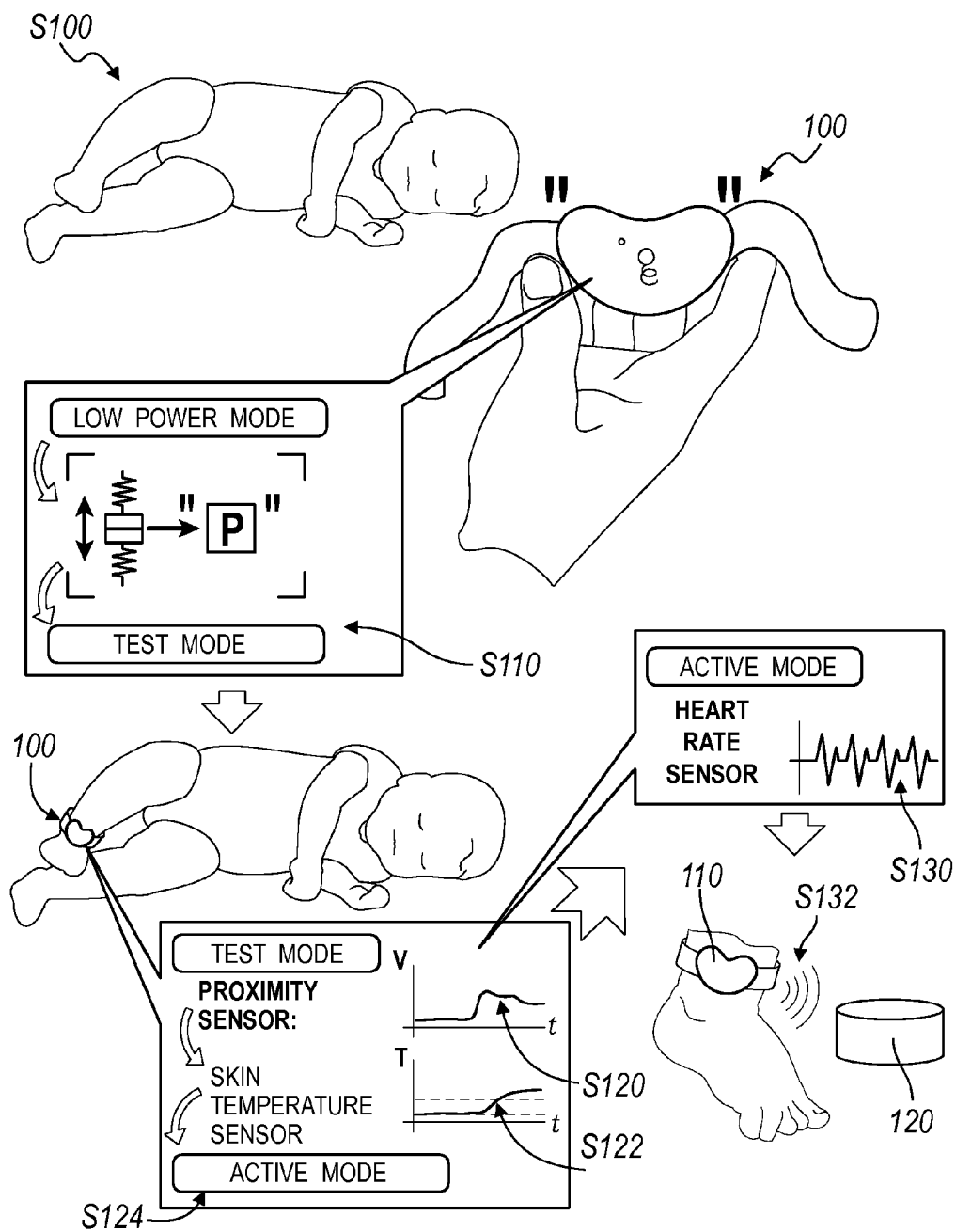
FIG. 6 is a flowchart representation of a first method in accordance with the invention.

As shown in FIG. 6, in one variation, the wearable device executes a first method S100 for changing a mode of a wearable device including: in response to detected motion of the wearable device, transitioning from a low-power mode into a test mode in Block S110; in the test mode, detecting a proximity of a surface to the wearable device Block S120, in the test mode, detecting a temperature of the surface Block S122; in the test mode, based on a temperature of the surface correlated to a human skin temperature, transitioning from the test mode into an active mode Block S124; in the active mode, sampling a heart rate sensor arranged within the wearable device Block S130, and, in the active mode, wirelessly broadcasting a value corresponding to an output of the heart rate sensor Block S132.

In this variation, the wearable device executes the first method S100 to sample a series of sensors within the wearable device in series to determine—automatically and substantially in real-time—if the wearable device has been placed on an infant. For example, the wearable device can execute the first method S100 to detect when the wearable device has been picked up, to arm the proximity sensor and/or the skin temperature sensor to detect a surface adjacent the wearable device, and to arm the wireless communication module to transmit a heart rate value substantially immediately (i.e., in real-time) once the wearable device is placed on the infant. Therefore, the wearable device can initiate the first method S100 when the wearable device is picked and just before the wearable device is placed on the infant, and the wearable device can complete the first method S100—and thus enter the active mode—substantially immediately after the wearable device is placed on the infant; with the wearable device now in the active mode, the wearable device can thus transmit various sensor data, such as a heart rate and a skin temperature, to the base station for publication on a guardian's mobile computing device (e.g., smartphone) and/or directly to the guardian's mobile computing device for presentation to the guardian with substantially minimal latency between when the wearable device is placed on the infant and when vitals data collected by the wearable device is presented to the infant's guardian through his mobile computing device.

In one example, when stationary and not in use (e.g., when stored on a shelf), the wearable device remains in the low-power setting in which the wireless communication module and the processor are deactivated. However, when the wearable device is picked up, a motion sensor (e.g., a tilt sensor)—coupled to a wake or interrupt pin of the processor—triggers the processor to activate and to enter the test mode, as in Block S110, such as in response to a voltage output of the motion sensor that exceeds a threshold voltage (or trigger voltage) corresponding to a threshold motion magnitude of the wearable device and a threshold interrupt voltage on the interrupt pin of the processor. Once in the test mode, the processor samples various sensors within the wearable device in series and/or in parallel to confirm that the wearable device was installed on an infant. Once in the test mode, the processor can also arm the wireless communication module to wirelessly deliver vitals data of the infant to the base station and/or to a mobile computing device paired with the wearable device. However, once detected motion of the wearable device ceases or falls below a threshold motion magnitude, the processor can initialize a timer (e.g., a two-second timer) for detecting further motion of the wearable device or for confirming installation of the wearable device on an infant before returning the wearable device back to the low-power mode.

In the test mode, the processor interfaces with a proximity sensor arranged within the wearable device to detect a surface adjacent the wearable device, as in Block S120. For example, once the processor enters the test mode, the processor can sample the proximity sensor (e.g., a capacitive proximity sensor) to detect a surface within a limited range (e.g., within 0.200") of the inner surface of the housing of the wearable device. If a surface is detected near the inner surface of the wearable device, such as adjacent or in contact with the inner surface of the housing, the processor can then interface with the skin temperature sensor to predict if the adjacent surface is human based on the skin temperature of the surface. However, if an adjacent surface is not immediately detected by the proximity sensor, the processor can initiate a timer (e.g., for one second) during which the processor samples the proximity sensor for an output indicating an adjacent surface, such as at a test rate (e.g., at 20 Hz); if an adjacent surface is not detected before the timer expires, the processor can transition the wearable device back into the low-power mode.

Once a surface is detected near the wearable device, the processor interfaces with the skin temperature sensor to detect a temperature of the adjacent surface, as in Block S122. For example, once the processor detects the adjacent surface, the processor can sample the skin temperature sensor (e.g., an infrared temperature sensor) to detect a temperature of the surface; if the detected temperature of the surface falls within a normal skin temperature range of an infant human (e.g., 98° F.±8° F.) (or if the skin temperature sensor detects a rising temperature on the adjacent surface indicative of human skin), the processor can automatically transition the wearable device into the active mode, as in Block S124. The processor can therefore interface with the skin temperature sensor and/or the heart rate sensor within the wearable device to predict placement of the wearable device on a human limb. However, if the temperature of the adjacent surface (or a change rate of outputs of the skin temperature sensor) does not indicate that the surface is human, the processor can initiate a timer (e.g., for one second) during which the processor samples the skin temperature sensor for an output indicating that the adjacent surface is human, such as at a test rate (e.g., at 20 Hz), if a suitable temperature is not detected before the timer expires, the processor can transition the wearable device back into the low-power mode.

In one alternatively variation, if the detected temperature of the surface falls within a normal skin temperature range of an infant human, the processor can sample the heart rate sensor to detect a heart rate through the surface before transitioning the wearable device into the active mode. Thus, once the temperature of the surface s suitably matched to a temperature of human skin, the processor can interface with the heart rate sensor to detect a heart rate through the skin surface. For example, the processor can sample the heart rate sensor to detect a heart rate of the corresponding infant; if the detected heart rate detected through the surface falls within a range of normal heart rates for infant humans, the processor can automatically transition the wearable device into the active mode, as in Block S124. However, if the heart rate sensor does not identify a heart rate through the surface, the processor can initiate a timer (e.g., for two seconds) during which the processor samples the heart rate sensor for an output corresponding to a heart rate, such as at a test rate (e.g., at 20 Hz), if a heart rate is not detected before the timer expires, the processor can transition the wearable device back into the low-power mode.

Once in the active mode, the processor can sample various sensors within the wearable device, as in Block S130, and cooperate with the wireless communication module to transmit raw and/or processed forms of sensor data to the base station and/or to a paired mobile computing device, as in Block S132. For example, once the wearable device enters the active mode, the processor can immediately sample the heart rate sensor, the skin temperature sensor, and an orientation sensor (in series) at an active-mode sample rate of 5 Hz (in Block S130). In this example, the processor can bundle these raw sensor data and a corresponding time stamp for the sensor sampling instance, and the wireless communication module can broadcast this bundle to the base station substantially in real-time with collection of these data such these data are received at the base station substantially in real-time with placement of the wearable device on the infant. At a subsequent sensor sampling instance (i.e., 200 ms later), the processor can again sample these sensors and bundle these data with a corresponding time stamp, and the wireless communication module can transmit this bundle to the base station.

The processor can also cooperate with the wireless communication module to detect a proximity of the base station and/or an affiliated mobile computing device to the wearable device. For example, the wireless communication module can support wireless bonds with multiple external devices, such as multiple base stations and multiple mobile computing devices affiliated with the infant's home, daycare, parents, grandparents, guardians, etc. When multiple bonded devices are within wireless range of the wearable device and/or wirelessly paired with the wearable device, the wireless communication module can selectively upload sensor data to one or a subset of these connected devices. In this example, the processor can analyze wireless signal strengths receives from local bonded devices or receive, from each of these local bonded devices, a value corresponding to a strength of a signal received from the wearable device, and the processor can select a particular bonded device exhibiting a greatest signal strength or receiving a signal of greatest strength from the wearable device, and the wireless communication module can upload sensor data exclusively to this device until the mobile computing device takes receipt of a wireless signal of greater strength is received from another local bonded device or the wireless communication module takes receipt of greater wireless signal strength value from another local bonded device. For example, the wireless communication module can initial wirelessly transmit various sensor data for a first series of sensor sample instances to the base station, and the wireless communication module can transition to transmitting a subsequent series of sensor sample instances to a mobile computing device within wireless range of the wearable device when wireless communication with the base station is lost or when a wireless signal from the mobile computing device to the wearable device (or from the wearable device to the mobile computing device) exceeds the wireless signal from the base station to the wearable device (or exceeds the wireless signal strength from the wearable device to the base station).

As described above, the wearable device can also automatically transition from the active mode (or the test mode) into the low-power mode, such as in response to receipt of a series of detected temperatures of the surface that fall outside of a preset range of human skin temperatures for a threshold time period. However, the wearable device can implement any other suitable method or technique to automatically transition the wearable device between various modes, such as a low-power mode, a test mode, and an active mode.

5. Base Station

Figure 3:
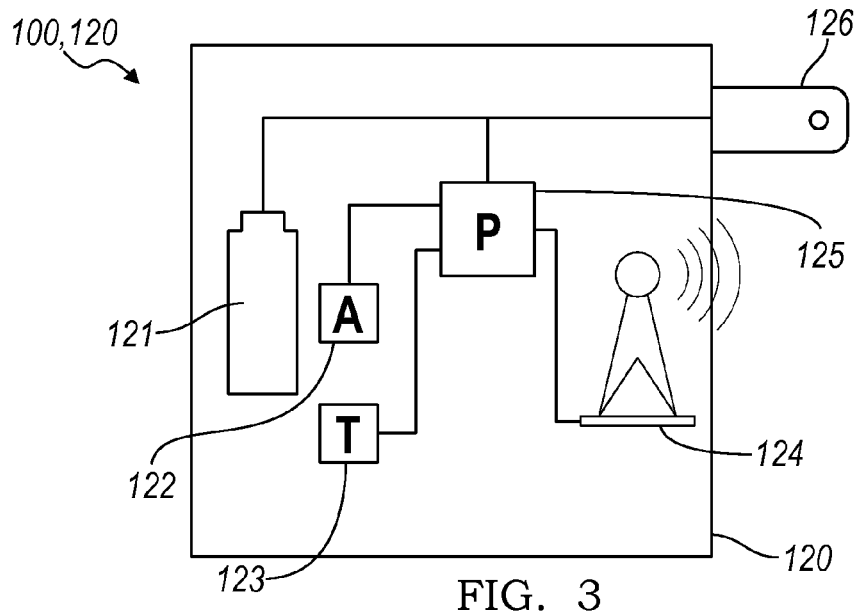
FIG. 3 is a schematic representation of one variation of the system.

As shown in FIG. 3, the base station of the system includes a battery 121, an accelerometer 122, an ambient temperature sensor 123, and a wireless receiver (or wireless communication module) 124. In one implementation, the base station collects local ambient data, wirelessly receives infant vitals data from the wearable device, and uploads merged infant and ambient data to an account associated with the infant, such as stored in a remote database linked to an application server. The application server can thus process these merged infant and ambient data to predict a future infant-specific event (e.g., a wake time from a sleeping period) and/or to generate an infant specific model (e.g., an infant-specific wakefulness model), as described below. The base station can additionally or alternatively transmit infant vitals data received from the wearable device and ambient data collected locally to a mobile computing device, such as a parent's smartphone or babysitter's tablet. A native infant monitoring application executing on the mobile computing device can thus manipulate the infant and ambient data locally to predict a future infant event, or the mobile computing device can upload these data to the remote database for processing by the application server.

In one implementation, the base station is configured to receive power primarily through a wall power receptacle (e.g., at 120 VAC @60 Hz), and the battery within the base station can function as power backup for the base station, such as in the event of a power outage or if the base station falls out of a wall power receptacle. For example, the base station can default to sourcing power through an integrated wall power plug 126 and automatically switch to battery power when power through the wall power plug is no longer available. In this implementation, a processor 125 within the base station can identify a power outage at the power receptacle if power through the wall power plug is lost but no acceleration is detected through an accelerometer within the base station to indicate that the base station was physically removed from the wall power receptacle. The processor within the base station can similarly determine that the base station has been removed from or fallen out of the wall power receptacle if power through the wall power plug is lost and an acceleration detected by the internal accelerometer occur at approximately the same times. In these implementations, the base station can transmit corresponding alarms to the mobile computing device (such as directly or through the application server) to notify a parent or guardian of the state of the base station. For example, for a battery charge expected to last at least eight hours, the base station can delay transmission of a power outage alert to the mobile computing device until the corresponding guardian of the infant is projected to wake up, such as based on an alarm setting set by the guardian on his mobile computing device, or until the guardian is determined to have woken up, such as based on detected motion of his mobile computing device. Alternatively, a native infant monitoring application executing on the guardian's mobile computing device can implement the foregoing methods and techniques to manage notifications received from the base station and/or to generate and queue such notifications based on data received from the base either directly or through the applications server. Yet alternatively, the application server can implement such methods and techniques to generate and queue base station-related notifications for delivery to one or more guardians affiliated with the infant (e.g., at noted in an account affiliated with the infant) based on data received from the base and/or from the mobile computing device.

The base station can include one or more other sensors, such as an ambient light sensor, a carbon monoxide sensor, a barometric pressure sensor, an ambient temperature sensor, a humidity sensor, an ambient sound meter (e.g., a microphone), etc., and the base station can sample one or more of these sensors over time. In one implementation, the base station limits data collection to periods during which the wearable device is in the active mode and within wireless range of the base station. Thus, the base station can thus aggregate infant vitals data received from the wearable device with ambient data collected by the base station (e.g., based on times that these data were recorded) before processing these data locally, before uploading these merged data to the application server, or before transmitting these data to a local mobile computing device for processing.

The base station can also generate and transmit alerts related to local ambient conditions, such as to the mobile computing device directly or to the application server. For example, the base station can detect a carbon monoxide level outside of a normal range, generate an alert for the detected carbon monoxide level, and transmit this alert to a mobile computing device associated with the infant's account, such as over Wi-Fi or cellular communication protocol. The base station can similarly generate alerts for detected ambient temperature levels that fall outside of a standard or guardian-selected temperature range (e.g., 62-85° F.) and transmit alerts to a local mobile computing device or to the application server accordingly. Alternatively, the application server or an instance of the native infant monitoring application executing on a guardian's mobile computing device can implement the foregoing methods or techniques to deliver notifications to the correspond guardian based on data received from the base station.

The base station can therefore include a wireless communication module that transmits ambient- and infant-related data to one or more mobile computing devices or to a computer network (e.g., the application server). For example, the base station can include a Wi-Fi card that establishes a wirelessly connection with a local Wi-Fi router to upload ambient condition data and infant vitals data to a remote database for storage in the infant's account. The base station can additionally or alternatively include a wireless communication module that communicates with a local computing device (e.g., smartphone, tablet, laptop computer) over cellular, Bluetooth, or other wireless communication protocol to offload ambient condition and infant vitals data.

The base station can also estimate proximities of one or more mobile computing devices and/or to one or more wearable devices to of the base station over time based on strengths of wireless signals communicated between these devices and the base station, such as described above. For example, the wireless communication module can correlate a wireless signal strength broadcast a local computing device with proximity of the computing device to the base station. In this example, when the wearable device is removed from the base station by more than a threshold distance or a signal broadcast from the wearable device is no longer detected, the base station can transmit an alert to the mobile computing device indicating that the wearable device is out of range of the base, and the base station can thus cease collection of local ambient data until the wearable device is again within the wireless range of the base station. The base station can thus restrict collection of ambient data specific to a location or space not occupied by the infant and therefore not sufficiently relevant to the infant. In this example, the base station can further communicate with the application server or with a local a mobile computing device (associated with the infant's account) directly to confirm that another computing device linked to the infant's account is within wireless range of the wearable device, is available to collect infant vitals data from the wearable device substantially in real-time, and/or incorporates one or more sensors to collect ambient condition data within or near the space or location occupied by the wearable device (and therefore the infant).

As described above, the base station can selectively transmit and receive data from select peripheral devices, such as the wearable device, a wireless router, and a limited set of mobile computing devices affiliated with the base station or with an infant's account linked to the base station. The base station can also encrypt infant vitals data or related notifications transmitted to various external devices, such as to maintain adequate health-related data privacy for the infant, and can decrypt encrypted communications received from these devices.

6. Alerts and Notifications

The system can transmit alerts and notifications to the mobile computing device when infant vitals data and/or ambient data suggests an external condition may interrupt the infant's current physiological state, that the infant is endangered, or that the infant may become endangered. For example, the system can transmit an alert to the mobile computing device if the infant's heart rate changes dramatically (e.g., by more than a threshold change) or if a characterization of infant motion changes, such as if the infant stops moving or breathing.

The system can also transmit—to one or more mobile computing devices—a notification including a prediction of a change to the infant's physiological state, as described below. For example, the system can generate a notification including a predicted wake time of the infant based on local temperature and humidity data collected by the base station during a nap period, the system can transmit a notification specifying the predicted wake time to a mobile computing device associated with a parent of the infant. Similarly, the system can update a virtual clock or other virtual timer within the user interface to show the predicted wake time of the infant. In another example, the system can determine that the infant is restless (or "fussy") based on accelerometer data received from the wearable device and can transmit a corresponding notification to the mobile computing device. The system can also predict symptoms or a health status change from infant vitals data and/or ambient condition data, the system can transmit a corresponding notification to the mobile computing device, such as to indicate that the infant shows signs of developing a cold or a fever. The system can further predict or identify development milestones of the infant over time, such as "first tooth" or "slept through the night."

To generate alerts and notifications, the system can create and maintain (e.g., update) an infant-specific model locally based on merged infant and ambient data. In one implementation, the system associates ambient data, such as temperature and humidity, with stimuli and pairs these stimuli with infant responses, such as heart rate and skin temperature. The system can then extrapolate trends in stimuli-response data series collected over time to generate an infant-specific model. As described below, the system can also collect manually-entered infant-related data, such as a response to an alert or notification (i.e., human feedback) entered by a guardian of the infant through a mobile computing device, and the system can implement supervised or semi-supervised machine learning to improve the infant-specific model over time based on such human feedback. Once model specific to the infant is thus created, the system can apply subsequent ambient condition and/or infant vitals data to the model to predict a current or future state or health status of the infant and to generate alerts, notifications, and user interface updates accordingly.

For example, the model can define a relationship between infant sleep time and local humidity and temperature (i.e., within the room in which the infant sleeps), the system can generate a notification indicating an expected wake time of the infant given a current local humidity and temperature, and then transmit the notification to the mobile computing device. In another example, the model can define a relationship between infant feeding schedules and infant behaviors, such as duration of crying stints as derived from acceleration data of the wearable device. In this example, a parent can manually enter infant feed times into the native infant monitoring application (i.e., the user interface), and the system can collect these feed data over time to build the infant-specific feed model and subsequently generate a notification suggesting a particular future feed time for the infant based on current infant behavior, current infant vitals data, and/or current ambient conditions proximal the infant. The system can also incorporate data from other infants, as described below, to correlate infant behavior and/or vitals with a change in infant health status, and the system can push an alert—to a mobile computing device associated with the infant's account—that the infant may be developing a sickness based on other infants who previously exhibited similar behaviors and symptoms and were diagnosed with one or more sicknesses.

However, the system can generate any other suitable type of alert or notification based on infant and ambient data specific to the infant and/or based on one or more other infants.

7. Data Streams

As described above, the system can collect ambient data from the base station and/or various local computing devices based on proximity of the wearable device the base station and/or to the local computing device(s). For example, the system can pair ambient data from a particular local device (e.g., the base station, a father's smartphone, or a grandparent's tablet, etc.) with infant vitals data received from the wearable device when a strength of a wireless signal received from the particular device exceeds strengths of signals received from other devices within wireless range of the wearable device or when a strength of a wireless signal received from the wearable device by the particular device exceeds the strength of a wireless signal received from the wearable device by other devices within wireless range of the wearable device, as described above. However, in this example, when the wearable device moves out of range of the particular device, the system can query other devices linked to the infant's account or identify other devices recently requesting wireless communication with the wearable device to elect an alternative device—local to the wearable device—from which to collect ambient condition data to be paired in time with infant vitals data collected at the wearable device.

The system can also systematically test for proximity of the wearable device to other devices associated with the infant's account and can queue particular other devices as backup nodes for collecting ambient condition data and/or for receiving infant vitals data from the wearable device if communication with the currently-elected device is lost, thereby enabling substantially seamless transition in collecting ambient condition data from devices proximal the wearable device and/or enabling substantially seamless transition in downloading infant vitals data at various devices proximal the wearable device. The system can therefore selectively prompt or enable a particular mobile computing device within range of the wearable device to retrieve infant vitals data from the wearable device and to collect ambient data, such as temperature and ambient light levels, through one or more sensors integrated into the particular mobile computing device. For example, the application server can communicate with the particular mobile computing device via an instance of the native infant monitoring application executing on the particular mobile computing device to trigger the mobile computing device to collect ambient noise and ambient light data through a microphone and a photosensor arranged within the mobile computing device, respectively. The instance of the native infant monitoring application can then pair these ambient conditions data with infant vitals data downloaded from the wearable device before uploaded these merged data series to the infant's account and/or before generating an infant-specific physiological model from these merged data series. The system can also selectively transition between collecting ambient condition data from various base stations located within a structure or space occupied by the infant based on the proximity of the wearable device to the base stations such that ambient condition data most relevant to the infant's location is consistently collected even if the infant moves or is moved throughout the structure or space over time. The system can therefore selectively collect local ambient condition data from a particular external computing device or from a particular base station based on proximity to the wearable device such that ambient data only most relevant (i.e., near) the infant is merged with infant vitals data collected by the wearable device.

Figure 7:
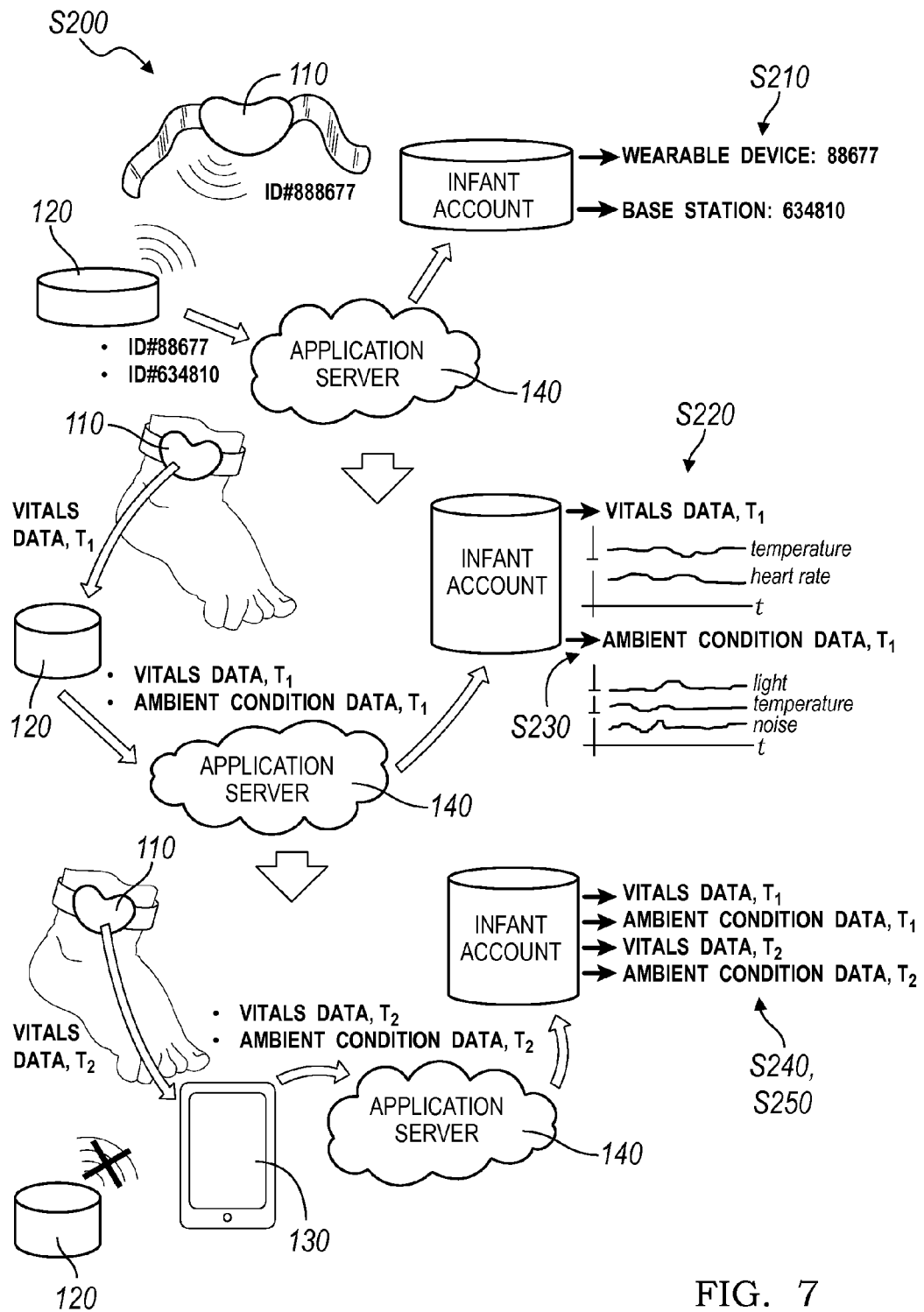
FIG. 7 is a flowchart representation of a second method in accordance with the invention.

Therefore, as shown in FIG. 7, one or more elements within the system (e.g., the application server) can execute a second method S200 for collecting vitals data of an infant and ambient condition data relevant to the infant, including: in response to receipt of wireless communication between a wearable device and a base station, linking the wearable device to an infant account associated with the base station in Block S210, during a first time period, receiving a first set of vitals data collected by the wearable device and a first set of ambient condition data collected by the base station in Block S220, based on a proximity of the wearable device to the base station during the first time period, storing the first set of ambient condition data with the first set of vitals data in the infant account in Block S230; during a second time period, receiving a second set of vitals data of the infant collected by the wearable device and a second set of ambient condition data collected by a mobile computing device wirelessly paired to the wearable device in Block S240; and, based on a proximity of the wearable device to the mobile computing device and a loss of wireless communication between the wearable device and the base station during the second time period, preferentially storing the second set of ambient condition data with the second set of vitals data in the infant account in Block S250.

Figure 8:
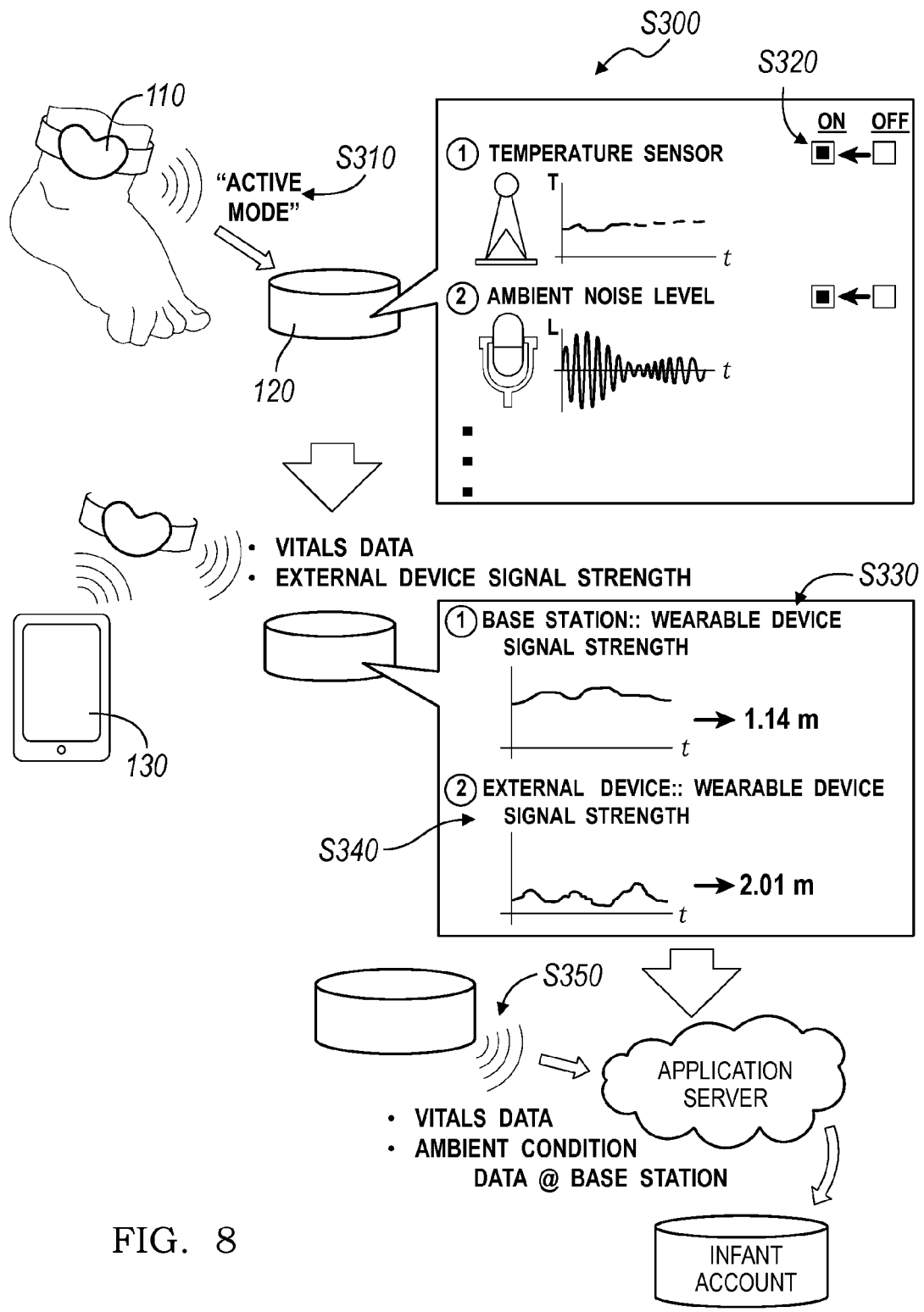
FIG. 8 is a flowchart representation of a third method in accordance with the invention.

Similarly, as shown in FIG. 8, one or more elements within the system can execute a third method S300 for collecting vitals data of an infant and ambient condition data relevant to the infant, including: at a base station, wirelessly receiving an active mode confirmation from a wearable device in Block S310, the active mode confirmation indicating transition of the wearable device from a low-power mode into an active mode; in response to receipt of the active mode confirmation, activating collection of ambient condition data through a sensor integrated into the base station in Block S320; estimating a first proximity of the base station to the wearable device based on a signal strength of wireless communications between the base station and the wearable device in Block S330; estimating a second proximity of a local external mobile computing device to the wearable device based on a signal strength of wireless communications between the local external mobile computing device and the wearable device in Block S340; in response to the second proximity exceeding the first proximity, selectively merging infant vitals data received from the wearable device with ambient condition data collected by the sensor in Block S350.

For example, the base station can execute the third method S300 to initiate data collection through various onboard sensors (e.g., the temperature sensor, the ambient light sensor, etc.) substantially immediately after the wearable device enters the active mode in response to determination of installation of the wearable device on a human (e.g., the infant). In this example, in response to entering the active mode the wearable device can automatically broadcast confirmation that is has entered into the active mode; the base station can receive this active mode confirmation in Block S310 and automatically begin to sample the onboard sensors to collect ambient condition data according to the active mode confirmation in Block S320. The base station can further communicate with the wearable device to estimate a proximity of the wearable device to the base station in Block S330, as described herein; the base station can also communicate with another mobile computing device within wireless range of the base station and/or within wireless range of the wearable device to receive an estimated distance between the mobile computing device and the wearable device or to calculate this distance internally, as in Block S340. The base station can thus selectively deactivate and reactivate collection of ambient data through sensors within the base—for grouping with infant vitals data relieved from the wearable device—based on the proximity of the base station to the wearable device relative to one or more other local mobile computing devices also linked to the infant's account, as in Block S350. In particular, the base station can sample its internal sensors to collect ambient condition data when conditions at the base station are substantially most relevant to the infant—as determined from a proximity of the wearable device to the base station; and the base station can cease collection of ambient condition data when conditions at the base station are less relevant to the infant than ambient conditions near another local mobile computing device—as determined from proximities of the wearable device to the base station and the local mobile computing device(s).

However, the base station, an instance of the native infant monitoring application executing on a mobile computing device linked to the infant's account, and/or the application server can function in any other way to selectively collect ambient condition data from devices within or connected to the system and to pair these ambient condition data with infant vitals data received from the wearable device.

8. Physiology Model and Predictions

As described above, the system can generate predictions for future changes in a physiological state of the infant based on one or more streams of infant vitals data and/or ambient conditions data collected by an external device substantially near the wearable device. For example, the system can apply a collective wakefulness model or an infant-specific wakefulness model (given sufficient infant-specific data to generate the infant-specific wakefulness model) to current vitals and ambient data streams to predict when the infant will wake from a nap.

Figure 9:
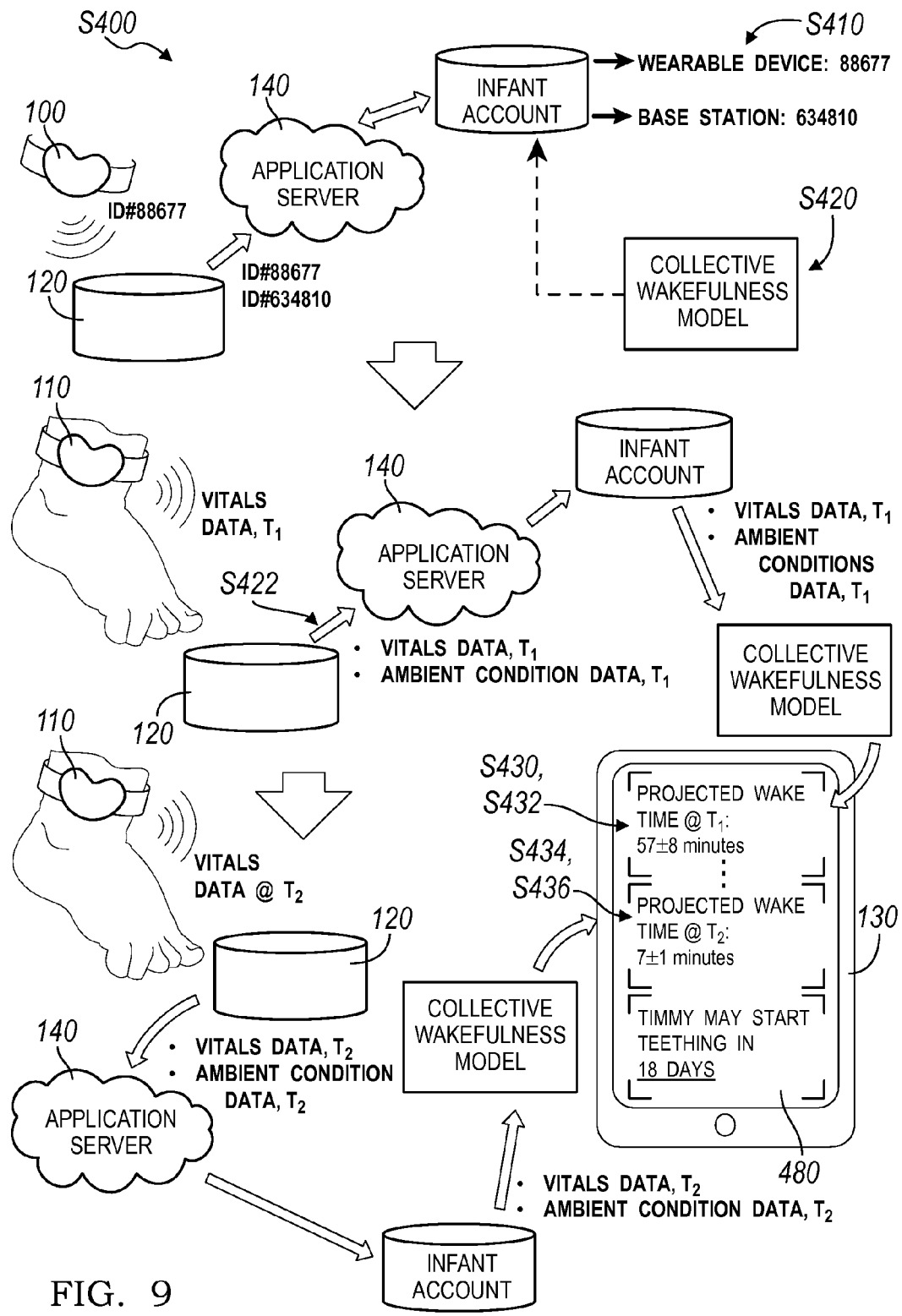
FIG. 9 is a flowchart representation of a fourth method in accordance with the invention.
Figure 10:
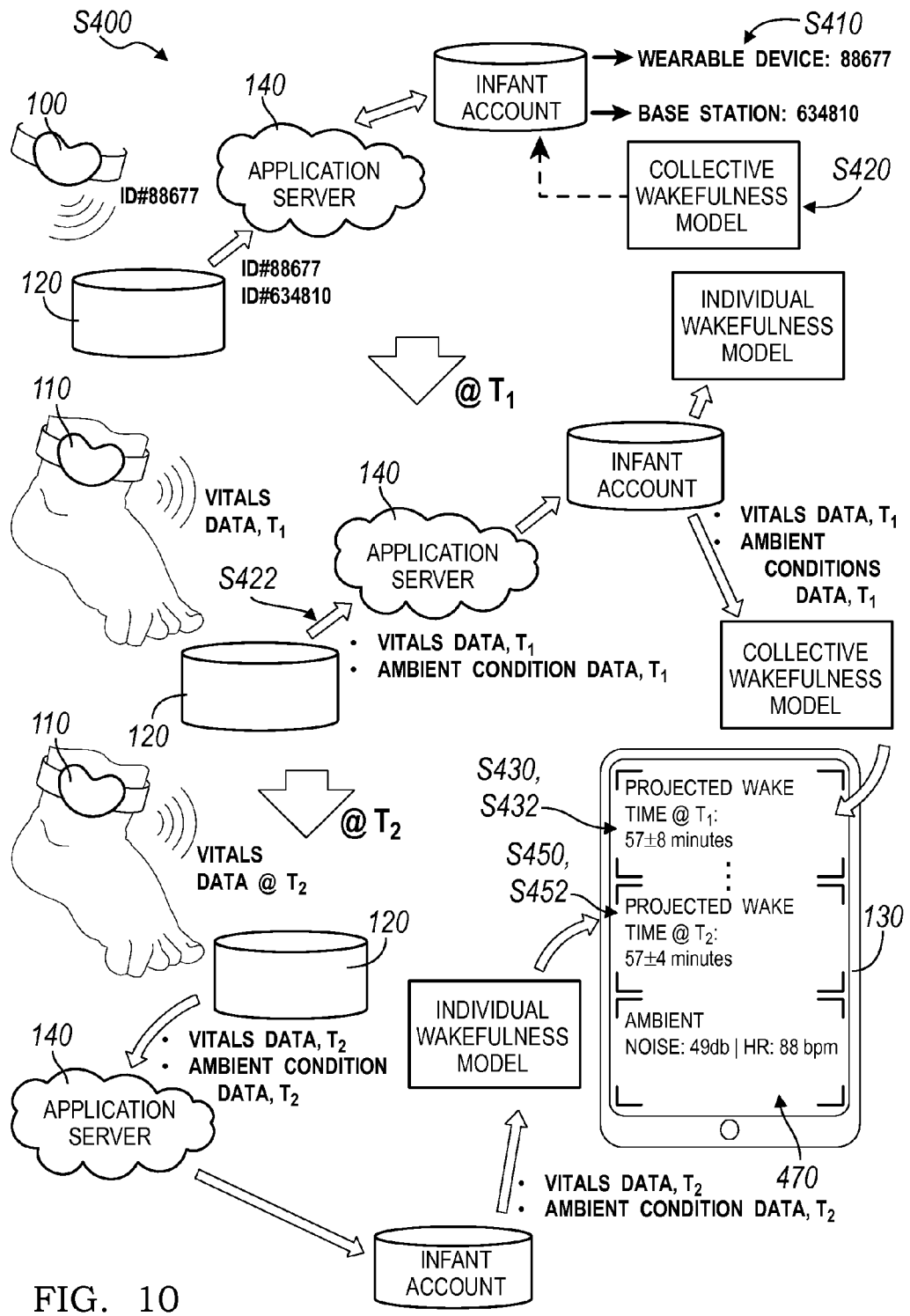
FIG. 10 is a flowchart representation of one variation of the fourth method.

As shown in FIGS. 9 and 10, one or more elements within the system can therefore execute a fourth method S400 for monitoring sleep of an infant, including: linking a wearable device to an account assigned to the infant in Block S410; assigning a collective wakefulness model to the infant for a first time period in Block S420, the collective wakefulness model generated from sleep data collected from a set of other infants; storing a first set of vitals data collected by the wearable device worn by the infant during first time period in Block S422; extrapolating, from the collective wakefulness model, a first wake time of the infant for a first sleep event during first time period based on data in the first set of vitals data in Block S430; prior to the first wake time, queuing the first wake time for transmission to a mobile computing device linked to the account for presentation to a guardian of the infant in Block S432; in response to expiration of the first time period, generating an infant-specific wakefulness model specific to the infant based on the first set of vitals data collected during the first time period and assigning the individual model to the infant for a second time period succeeding the first time period in Block S440; extrapolating, from the infant-specific wakefulness model, a second wake time of the infant for a second sleep event during the second time period based on a second set of vitals received from the wearable device during the second time period in Block S450, and prior to the second wake time, queuing the second wake time for transmission to the mobile computing device for presentation to the guardian in Block S452.

As shown in FIGS. 9 and 10, the system can also execute one variation of the fourth method S400 including: linking a wearable device to an account assigned to the infant in Block S410, selecting a collective wakefulness model for the infant, the collective wakefulness model generated from sleep data collected from a set of other infants in Block S420, at a first time during a sleep event of the infant, extrapolating, from the collective wakefulness model, a predicted wake time of the infant for the sleep event based on a first set of vitals data received from the wearable device worn by the infant during the sleep event in Block S430, prior to the predicted wake time, transmitting the predicted wake time to a computing device associated with the account for presentation to a guardian of the infant in Block S432; at a second time during the sleep event succeeding the first time, extrapolating, from the collective wakefulness model, a revised predicted wake time of the infant for the sleep event based on a subsequent set of vitals data received from the wearable device during the sleep event in Block S434, and prior to the revised predicted wake time, transmitting the revised predicted wake time to the computing device for presentation to the guardian in Block S436.

8.1 Infant's Account

Block S410 of the fourth method S400 recites linking a wearable device to an account assigned to the infant. Generally, Block S410 functions to generate a new account and to assign the new account to the infant, such as upon a first use of the wearable device. For example, a parent (or other guardian) of the infant can purchase a kit including the base station and the wearable device, unpackage the base station and the wearable device, and access an native application store through his mobile computing device (e.g., smartphone) to install the native infant monitoring application on his mobile computing device. Once the base station and the wearable device are powered on (e.g., when the wearable device enters the test mode of the active mode), the native infant monitoring application can automatically establish a wireless connection or "pair" with each of the base station and the wearable device, and the wearable device can wirelessly pair with the base station. With the native infant monitoring application, the base station, and the wearable device now wirelessly connected, the native infant monitoring application and/or the base station can establish a connection to the application server. For example, the native infant monitoring application can collect unique IDs from the mobile computing device, the base station, and/or the wearable device and pass these unique IDs to the native application; the native application can then generate a new private account linked to the instance of the native infant monitoring application executing on the parent's mobile computing device via the corresponding unique ID, linked to the particular base station via the corresponding unique ID, and/or linked the particular wearable device via the corresponding unique ID. The account can be private to the application server and function as a private repository for vitals and ambient condition data specific to the infant. Alternatively, the account can be accessible by the parent—such as through the user interface executing within the instance of the native infant monitoring application—to review various infant-related data, infant physiology models, etc. In this implementation, multiple additional devices can be linked to the account, such as additional base stations (e.g., other base stations arranged in other locations or rooms frequented by the infant), additional wearable devices (e.g., other wearable devices operated by other guardians of the infant), and other mobile computing devices (e.g., smartphones and/or tablets associated with another parent, grandparent, babysitter, etc. of the infant) executing additional instances of the native infant monitoring application.

However, any other element within the system can execute Block S410 in any other suitable way to assign a private or user-facing account to the infant.

8.2 Collective Wakefulness Model

Block S420 of the fourth method S400 recites assigning a collective wakefulness model to the infant for a first time period in Block S420, the collective wakefulness model generated from sleep data collected from a set of other infants. Generally, Block S420 functions to select a collective wakefulness model for application to the infant's vitals and ambient condition data to predict a future time at which the infant will awake from a nap. The system can therefore execute Block S420 to select a collective wakefulness model that can be applied to infant data to generate a prediction about a future physiological change (e.g., a degree of wakefulness) of the infant despite a lack of related data previously collected from the infant. For example, the system can execute Blocks S420, S430, and S432 during a first use of the wearable device to make predictions about when the infant will wake from a nap, and the system can later execute Block S440 to generate a wakefulness model specific to the infant once a sufficient volume of data specific to the infant has been collected.

The system can implement Block S420 by selecting a generic collective wakefulness model trained from vitals data, ambient data, and known sleep states of various other infants (or other users) and pass this generic collective wakefulness model to an instance of Block S430.

Alternatively, the system can execute Block S420 by selecting, for the infant, a particular collective wakefulness model from a set of available collective wakefulness model, such as based on one or more qualities or characteristics of the infant. For example, the user interface can prompt a guardian to enter a birthdate, an age, a gender, a health condition, or any other quality or characteristic of the infant, and the system can select a particular collective wakefulness model generated from vitals and ambient data of other infants characterized by the same or similar age, gender, health condition, or any other quality. In a similar example, the system: can retrieve an age of the infant, such as stored in the infant's account or entered by a guardian through the user interface; correlate the age of the infant with a particular development stage; select a default collective wakefulness model generated from sleep data collected from other infants during the same particular development stage, and then assign this default collective wakefulness model to the infant for the duration of the first development stage of the infant, as in Block S420.

The system can additionally or alternatively assemble data of other infants of similar qualities or characteristics at the infant and/or collected during development stages similar to those of the infant and then train a collective wakefulness model for the infant based on this assemblage of data.

The system can also select (or generate) a collective wakefulness model for the infant based on a limited volume of vitals and/or ambient data collected from the wearable device installed on the infant or from the base station or external computing device wirelessly connected to the wearable device, respectively. For example, the system can execute any of the foregoing methods or techniques to select a generic collective wakefulness model for initial application to infant data collected during a first napping period of the infant during a first use of the wearable device on the infant, implement Block S422 to collect vitals and ambient data from the wearable device and the base station, respectively, and then repeat Block S420 to identify other infants exhibiting similar vitals during similar ambient condition. In particular, the system can associate the infant with a cluster of other infants in a collection of other infants based on an initial set of vitals and/or ambient condition data collected from the wearable device and/or the base station, respectively, and the system can then select a particular collective wakefulness model generated from sleep data collected from infants in this cluster of other infants. Similarly, the system can execute a second instance of Block S420 to generate a custom collective wakefulness model for the infant based on existing vitals and ambient data of other infants in the cluster of other infants. The system can then assign this custom or particular collective wakefulness model to the infant for some duration, such as until additional infant data is available to refine the cluster of related other infants and to generate a refined custom collective wakefulness model for the infant accordingly or until sufficient data has been collected from the infant to generate a wakefulness model specific to the infant from (wholly or predominantly) these infant-specific data.

The collective wakefulness model assigned to the infant can therefore be trained from existing vitals and ambient condition data collected from other infants, such as during known physiological (e.g., sleep) states. For example, the collective wakefulness model can be generated from time series of heart rate, skin temperature, motion (e.g., acceleration), orientation, ambient temperature, ambient light level, ambient noise level, ambient humidity level, and/or ambient air quality (e.g., carbon monoxide level), etc. and a time series of known physiological states (e.g., asleep, awake, and/or waking) of a multitude of other infants, such as according to non-parametric Gaussian processing techniques. However, the collective wakefulness model can incorporate any other type or series of data collected from any other number of infants or other infants over time.

8.3 Data Collection

Block S422 of the fourth method S400 recites storing a first set of vitals data collected by the wearable device worn by the infant during first time period. Generally, the system can execute Block S422, as described above, to collect infant vitals data from the wearable device and ambient condition data from one or more base stations and/or mobile computing devices local to the wearable device (and therefore local to the infant). For example, the application server (or a database within or linked to the application server) can execute Block S422 to collect a time series of heart rate data, a time series of skin temperature data, and a time series of motion data collected by the wearable device and routed through a local base station linked to the infant's account. In this example, the application server can also receive a first set of ambient condition data including a time series of ambient temperature data, a time series of ambient noise data, a time series of ambient light data, and a time series of ambient humidity data collected by the base station, and the application server can store these ambient condition data with vitals data collected at or around the same time, as described above.

8.4 Predicted Wake Times—Collective Wakefulness Model

Block S430 of the fourth method S400 recites extrapolating, from the collective wakefulness model, a first wake time of the infant for a first sleep event during first time period based on data in the first set of vitals data, and Block S432 of the fourth method S400 recites prior to the first wake time, queuing the first wake time for transmission to a mobile computing device linked to the account for presentation to a guardian of the infant. Generally, the system executes Block S430 to predict a future time that the infant will wake from a current sleep (or napping) period by applying a current time series of infant vitals and/or ambient condition data collected according to Block S422 to the collective wakefulness model selected in Block S420. The system then executes Block S432 to deliver a notification indicated the predicted wake time to a guardian of the infant via a corresponding a mobile computing device noted in the infant's account, as described above, and/or to update an instance of the user interface rendered within an instance of the native infant monitoring application executing on a mobile computing device linked to the infant's account.

In one implementation, in Block S422, the system begins collecting vitals and ambient data through the wearable device and the base station or a related local mobile computing device as soon as the wearable device enters the active mode (as described above in the third method S300), as described above. Based on sensors operable within the wearable device and the base station or the local mobile computing device, the system can assemble time series of heart rate, skin temperature, motion (e.g., acceleration), orientation, ambient temperature, ambient light level, ambient noise level, ambient humidity level, and/or ambient air quality, etc. substantially in real-time and apply the available time series to the collective wakefulness model in Block S430 to extrapolate a predicted wake time of the infant from the collective wakefulness model, such as according to a non-parametric Gaussian processing technique.

Once the system generates a first prediction for the wake time of the infant, the system can execute Block S432 to queue or notification for delivery to one or more mobile computing devices linked to the infant's account. For example, the system can identify one or more mobile computing devices noted in the infant's account and within a threshold range of the wearable device, such as within 300 feet of the wearable device. The system can thus generate a notification indicating the predicted wake time and push this notification to the identified mobile computing devices. Alternatively, instances of the notification executing on various mobile computing devices linked to the infant's account can pull this wake time prediction from the application server and update corresponding instances of the user interface to visually present the predicted wake time.

In one variation, the system further executes Block S434 of the fourth method S400, which recites, at a second time during the sleep event succeeding the first time, extrapolating, from the collective wakefulness model, a revised predicted wake time of the infant for the sleep event based on a subsequent set of vitals data received from the wearable device during the sleep event, and Block S436, which recites, prior to the revised predicted wake time, transmitting the revised predicted wake time to the computing device for presentation to the guardian in Block S436. Generally, the system can execute Block S434—much like Block S430—to update or revise the predicted wake time of the infant from the current nap period based on additional infant vitals and/or ambient condition data collected by the wearable device and/or the base station or local mobile computing device, respectively. Once the revised wake time is thus determined, the system executes Block S436 to present this revised time through one or more mobile computing devices affiliated with the infant's account. Therefore, in Blocks S434 and S436, the system can repeat the fourth method S400s and techniques of Blocks S430 and S432, respectively, based on additional data collected from the infant and the infant's environment. The system can continue to update the predicted wake time of the infant through the sleep period, such as at a rate of 0.1 Hz or with each addition set of infant vitals and ambient data received.

The system can therefore execute Blocks S430 and S432 to generate a predicted wake time of the infant early in sleep period. For example, the system can execute Block S430 within five seconds of receiving a first set of infant vitals and ambient condition data (e.g., within five seconds of the wearable device entering the active mode) in Block S420 or within five seconds of determining that the infant has fallen asleep based on heart rate, motion, and/or other infant vitals data received from the wearable device in Block S420. However, due to the limited volume of vitals and ambient data available for current period in which the infant is or is predicted to be asleep, the predicted wake time extrapolated from the collective wakefulness model based on this limited volume of data may be associated with relatively large first variance or relatively wide first confidence band (e.g., ±9 minutes for a sleep period projected to last an additional 57 minutes). However, as additional infant vitals and ambient condition data is collected during the sleep period and as the real wake time of the infant approaches, a revised predicted wake time of the infant generated by the system, such as in Block S434, may be associated with a variance less than the first variance or a confidence band narrow than the first confidence band (e.g., ±33 seconds for a sleep period projected to last an additional 7 minutes).

The system can therefore systematically repeat Block S434 to revise the predicted wake time of the infant based on the collective wakefulness model and additional infant vitals and ambient condition data; the system can also systematically repeat Block S436 to push or upload revised wake times to one or more corresponding mobile computing devices for review by a guardian affiliated with the infant.

8.5 Infant-Specific Wakefulness Model

Block S440 of the fourth method S400 recites training a new wakefulness model specific to the infant based on the first set of vitals data collected during the first time period and based on wakefulness states of the infant during sleep events in the first time period determined from wakefulness states of other infants in the set of other infants. Block S440 can similarly recite, in response to expiration of the first time period, generating an infant-specific wakefulness model specific to the infant based on the first set of vitals data collected during the first time period and assigning the individual model to the infant for a second time period succeeding the first time period. Generally, the system can execute Block S440 to generate an infant-specific wakefulness model (or "individual wakefulness model") based on a volume of infant vitals and ambient condition data collected from the wearable device and the base station and/or local mobile computing device over time, such as to the exclusion of available vitals and/or ambient condition data of other infants.

In one implementation, the system retrieves stored data corresponding to discrete sleep periods completed by the infant over a period of time, such as over a period of one week. For each discrete sleep period, the system amasses one or more time series including heart rate, skin temperature, motion, orientation, ambient temperature, ambient light level, ambient noise level, ambient humidity level, and/or ambient air quality, etc. The system also characterizes stages within each discrete sleep period—such as awake, falling asleep, asleep, waking, and/or awake—such as based on existing models for determine physiological states related to sleep and one or more times series within during a discrete period. For example, the system can identify various physiological stages of the infant during a particular sleep period based on magnitudes, directions, and/or patterns in acceleration data collected by an accelerometer integrated into the wearable device worn by the infant during the particular sleep period. The system can then merge these like time series across the multiple discrete sleep periods and extrapolate trends in or relationships between each data type and determined physiological stages of the infant over time. For example, the system can aggregate heart rate data and physiological state data of the infant across multiple sleep periods over the course of one week to characterize (or "model") a relationship between heart rate and a projected time that the infant will wake from a sleep period. In this example, the system can also: aggregate skin temperature data and physiological state data of the infant across multiple sleep periods over the course of the week to characterize a relationship between skin temperature and a projected time that the infant will wake from a sleep period; aggregate motion data and physiological state data of the infant across multiple sleep periods over the course of the week to characterize a relationship between motion and a projected time that the infant will wake from a sleep period; aggregate ambient light data and physiological state data of the infant across multiple sleep periods over the course of the week to characterize a relationship between ambient light levels and a projected time that the infant will wake from a sleep period; aggregate ambient temperature data and physiological state data of the infant across multiple sleep periods over the course of the week to characterize a relationship between ambient temperature levels and a projected time that the infant will wake from a sleep period; and aggregate ambient humidity data and physiological state data of the infant across multiple sleep periods over the course of the week to characterize a relationship between ambient humidity levels and a projected time that the infant will wake from a sleep period; etc.

The system can therefore generate an infant-specific wakefulness model that can be applied to one or more time series of current infant vitals data and/or one or more time series of current ambient condition data to predict when the infant will awake from his current nap.

However, the system can execute Block S440 to generate a wakefulness model specific to the infant according to any other method or technique (e.g., non-parametric Gaussian processing) and based on any other one or more data types (e.g., heart rate, skin temperature, ambient light level etc.) collected over any other number of sleep periods and/or over any other duration of time.

In one implementation, the system executes Block S440 upon receipt of a sufficient volume (e.g., or a threshold volume) of vitals data of the infant over a series of sleep events, such as a total of forty hours of infant vitals data collected over a sequence of consecutive sleep events. The system can additionally or alternatively execute Block S440 to generate a first wakefulness model specific to the infant upon expiration of a preset period of time, such as following a first use of the wearable device or following expiration of assignment of the collective wakefulness model to the infant. For example, Block S420 can assign the collective wakefulness model to the infant for a duration of one week, which corresponds to a first one-week-long development stage of the infant. Upon expiration of the first one-week-long development stage, the system can execute Block S440 to generate the infant specific wakefulness model based on vitals and/or ambient data collected on behalf of the infant during the first development stage. Therefore, in response to expiration of the first development stage, the system can generate the infant-specific wakefulness model specifically for the infant and assign the infant-specific wakefulness model to the infant for a second development stage of the infant succeeding the first development stage. However, the system can assign the collective wakefulness model and the first infant-specific wakefulness model to the infant for any other duration of time or for any other present or determined development stage of the infant.

In the foregoing implementation, the system can further repeat Block S440 upon expiration of the second development stage—and upon commencement of a third development stage—to generate a second infant-specific wakefulness model based on infant vitals and ambient data collected on behalf of the infant during the second development stage, such as to the exclusion of all or a portion of infant vitals and ambient data collected during the first development stage. Block S440 can thus assign the second infant-specific wakefulness model to the infant for the third development stage of the infant succeeding the second development stage. The system can cyclically repeat Block S440 over time as subsequent development periods (of the same or varying duration) expire (or are about to expire) such that wakefulness models assigned to the infant over time remain current (and not necessarily subject to infant data collected during a previous development stage during a period of rapid development of the infant).

8.6 Predicted Wake Times—Infant-Specific Wakefulness Model

Block S450 of the fourth method S400 recites extrapolating, from the infant-specific wakefulness model, a second wake time of the infant for a second sleep event during the second time period based on a second set of vitals received from the wearable device during the second time period, and Block S452 of the fourth method S400 recites, prior to the second wake time, queuing the second wake time for transmission to the mobile computing device for presentation to the guardian in Block S452. Generally, the system can implement methods and technique similar to Block S430 to predict a future wake time of the infant during a current nap period based on current vitals and/or ambient collected on behalf of the infant and the infant-specific wakefulness model currently assigned to the infant. The system can implement methods and technique similar to Block S432 to deliver this projected wake time of the infant to one or more computing devices associated with the infant's account.

The system can further implement methods or techniques similar to Blocks S434 and S436, described above, to extrapolate, from the infant-specific wakefulness model, a revised second wake time of the infant for the current sleep event based on a third set of vitals received from the wearable device succeeding receipt of the second set of vitals during the second time period.

8.7 Secondary Notifications

As shown in FIG. 10, one variation of the fourth method S400 further includes Block S470, which recites, in response to ambient noise in the time series of ambient noise data exceeding a threshold ambient noise valve, transmitting an alert to the mobile computing device. Block S470 can additionally or alternatively recites transmitting a current heart rate and a current skin temperature of the infant to an affiliated computing device for presentation to a guardian of the infant. Generally, the system can execute Block S470 to deliver infant vitals and/or ambient conditions data to one or more mobile computing devices affiliated with the infant's account substantially in real-time, such as described above. For example, the application server can execute Block S470 to push a current heart rate to an instance of the user interface within an instance of the native infant monitoring application executing on a related mobile computing device, and the instance of the native infant monitoring application can update the user interface to reflect the current heart rate of the infant received from the application server.

8.8 Long Term Trends

As shown in FIG. 9, one variation of the fourth method S400 includes Block S480, which recites extracting a development trend of the infant from the second set of vitals data and the third set of vitals data and predicting a date of a future development event of the infant based on a comparison of the development trend to a development history of an other infant. Generally, the system can execute Block S480 to predict a future time of a significant development event of the infant—such as a teething event, a rollover event, a crawling event, a walking event, or a first word event—of the infant based on vitals data of the infant collected through the wearable device (or multiple wearable devices) over time.

In one implementation, the system tracks trends in heart rate, breathing rate and/or breathing pattern, motion types and/or amplitudes, skin temperature, etc. of the infant over time and matches one or more of these vitals trends to one or more vitals trend of one or more other infants associated with a known timing of one or more significant development events. In this implementation, the system can match the infant to a cluster of other infants based on these trends in infant, estimate a time (e.g., date) of a future significant development event of the infant based on an average timing of the significant development event within the selected cluster of other infants, and then communicate this estimated data of the significant development event to one or more guardians of the infant. For example, the application server can generate and maintain a timeline of life events for the infant and update this timeline with past development events of the infant, such as development events manually entered by one or more guardians of the infant and/or development events automatically detected by the system based on infant vitals data collected over time. In this example, the system can also update this timelines with projected dates of future development events. In this example, the system can calculate a tolerance or variance for a predicted time of a future development event of the infant (e.g., ±1 day, ±3 days, ±1 week, etc.) and can present this tolerance or variance for the development event as a time band within the timeline. The timeline can thus be accessed through an authorized instance of the native application executing on a mobile computing device. However, the system can execute Block S480 of the fourth method S400 in any other way to predict a time of a future development event of the infant and to present this predicted time for the development event to one or more guardians of the infant.

9. User Interface and Mesh Network

The interface executes on the mobile computing device and is configured to display a projected wake time of the infant from a current sleep event and infant-related alerts based on infant vitals data collected by the wearable device and/or ambient conditions data collected by the base station. The user interface can be implemented within an instance of a native infant monitoring application executing on a mobile computing device, such as a smartphone or tablet associated with the infant's account. The native infant monitoring application can thus display alerts, notifications, infant vitals, and ambient conditions related to the infant substantially in real-time, at a preferred time set by the system, or in response to a detected event (e.g., once an alarm clock on the mobile computing device triggers). The user interface can also record manually-entered responses to various alerts, notifications, etc. presented on the mobile computing device, and the user interface can communicate this manual feedback back to the application server, the base station, or other component within the system to teach an infant-specific physiology model (e.g., through supervised or semi=supervised machine learning), to augment a development event timeline of the infant, etc.

The native infant monitoring application can further function as an interface for access to the infant's account. For example, as described above, the application server can store and maintain a private account specific to the infant, and the application server can aggregate and store infant vitals data, ambient condition data, one or more infant-specific physiology models, etc. for the infant with or within the infant's account. Furthermore, the application server can store a unique ID of the wearable device, a unique ID of the base station, and/or unique IDs (or phones numbers, email addresses, etc.) for various authorized mobile computing devices with the infant's account such that new ambient and/or infant vitals data collected by the wearable device and ambient condition data collected by the base station and one or more external mobile computing devices can be or routed to the infant's account based on these unique IDs.

The application server can also store one or more usernames and passwords associated with the infant's account such that one or more guardians of the infant can access data contained within the infant's account by supply an authorized username and password through an instance of the user interface executing on a corresponding mobile computing device. For example, the application server can store—with the infant's account—a first username for the infant's mother and a second username for the infant's father as corresponding to primary profiles for access to data within the infant's account. The infant's mother can thus log in to the infant's account via an instance of the native infant monitoring application executing on her smartphone (or other device) set to add secondary users (with limited data access) to the infant's account, to assign data permissions for secondary users with the infant's account, to access notifications related to the infant, to manually upload feeding, sleeping, and other infant-related data, etc. The infant's father can similarly log in to the infant's account via an instance of the native infant monitoring application executing on his smartphone to similarly access infant data and/or to supply similar information to the system.

In one example, a parent (or other guardian) with primary access to the infant's account can review substantially all infant-related data through an instance of the native infant monitoring application executing on his computing device. The parent can also add a grandparent, a nanny, a babysitter, a daycare representative, a doctor, and/or any other suitable entity to the infant's account as a secondary (or tertiary) user. The parent can then select various data permissions for each secondary (or tertiary) user thus added to the infant's account. In this example, the parent can set the doctor's account to transmit health-related notifications to the doctor's smartphone and to upload relevant infant vitals data to a secure medical record (or hospital) network. The parent can also set the babysitter's account to receive all notifications and alerts not related to the infants medium- and long-term health and to enable the babysitter to manually enter feeding and sleeping times through an instance of the native monitoring application executing on his smartphone when the babysitter's smartphone is within wireless range of the wearable device and/or within wireless range of the base station. In this example, the parent can additionally or alternatively set the daycare representative's profile to enable manual upload of infant vitals data and to enable access to notifications and alerts through an instance of the native monitoring application executing on his smartphone or other computing device when the wearable device assigned to the infant is within wireless range of the daycare representative's computing device and/or within wireless range of a base station associated with the daycare facility. However, a guardian of the infant with primary access to the infant's account can access the infant's account to set read and write permissions of any other suitable type for any other type of secondary (or tertiary) user account assigned to the infant's account.

An instance of the native infant monitoring application executing on a guardian's computing device can also enable the guardian to associate or link additional base stations to the infant's account (or to the wearable device assigned to the infant). For example, a parent can access the native infant monitoring application executing on his smartphone to select a base station from a set of base stations currently active or online—such as based on an address, a GPS location, an affiliated business entity, or an IP address, etc. —and to specify a particular relationship between the infant's account and the selected base station. In this example, the parent can set a first selected base station located in the infant's nursery as a primary base station and can set a second selected base station located in the kitchen of the infant's primary residence as a secondary base station. In this example, the parent can also set a third selected base station located in the infant's grandparent's house, a fourth selected base station located in the infant's doctor's office, a fifth selected base station located in the infant's in a daycare facility, etc. as tertiary base stations for the infant. The parent can thus authorize the system to write ambient condition data collected through these primary, secondary, and tertiary base stations to the infant's account; the parent can thus further authorize the wearable device to offload infant vitals data to these primary, secondary, and tertiary base stations when the wearable device is within wireless range. The native infant monitoring application can also enable the parent to set permissions and restrictions for communication of infant related data through various base stations, such as similar selection of read/write permissions for individual user profiles linked to the infant's account, as described above.

The parent of the infant can also similarly interface with the native infant monitoring application to define if, how, and/or when an external computing device associated with the infant's account (e.g., a daycare representative's smartphone) can retrieve infant vitals data from the wearable device and write these infant vitals data to the infants account. For example, the parent can set: a first base device arranged in the infant's nursery as a primary recipient for infant vitals data collected by the wearable device; her own smartphone as a secondary data recipient for infant vitals data when the first base station is not within wireless range of the wearable device; and her spouse's smartphone as a tertiary data recipient for infant vitals data when the first base station and her smartphone is not within wireless range of the wearable device. The parent can further set a base station arranged in a daycare facility, a base station arranged in a grandparent's house, a grandparent's smartphone, a base station arranged in a hospital, a doctor's smartphone, etc. as lower-priority data recipients for infant vitals data when the parents' smartphones are not within wireless range of the wearable device. For example, when the infant is in his nursery, the nursery base station can collect data from the wearable device, but when the infant moves or is carried beyond the wireless range of the nursery base station but remains within or enters a wireless range of the parent's smartphone and a grandparent's smartphone, the parent's smartphone can collect infant vitals data from the wearable device until the wearable device again out of wireless range of both the parent's smartphone and the nursery base station, at which point the grandparent's smartphone can collect infant vitals data from the wearable device. Furthermore, in this example, when the parent brings the infant to a daycare facility, the instance of the native infant monitoring application executing on the parent's smartphone can default to collecting infant vitals data and uploading these data to the infant's account until the parent leaves the daycare facility, at which point a base station within the daycare collects infant vitals data from the wearable device data, as authorized by the parent in the infant's account. In this example, a daycare representative's smartphone can further collect infant vitals data from the wearable device data when the infant moves out of wireless range of the daycare base device.

In the foregoing implementation, a specific base station, smartphone, or other device tasked with data retrieval from the wearable device can also collect ambient local data that can be merged with infant vitals data ether locally or remotely at the application server (e.g., based on similar timestamps between the ambient data and the vitals data), as described above. However, for multiple base stations, smartphones, and/or other devices associated with the infant's account and within wireless range of the wearable device at any given time, the system can retrieve ambient data from these multiple relevant devices, such as on a per-sensor basis, and merge these sensor data streams with infant vitals data in the infant's account. For example, for ambient data received from a first parent's smartphone that indicates low ambient light level and a temperature over 90° F. and for ambient data received from a second parent's smartphone that indicates average ambient light level and a temperature around 72° F., the application server can determine that the first parent's smartphone is in the first parent's pocket and therefore remove the ambient data stream corresponding to the first parent's smartphone from the infant's account since this data stream is not substantially expressive of current ambient conditions proximal the infant.

Figure 4:
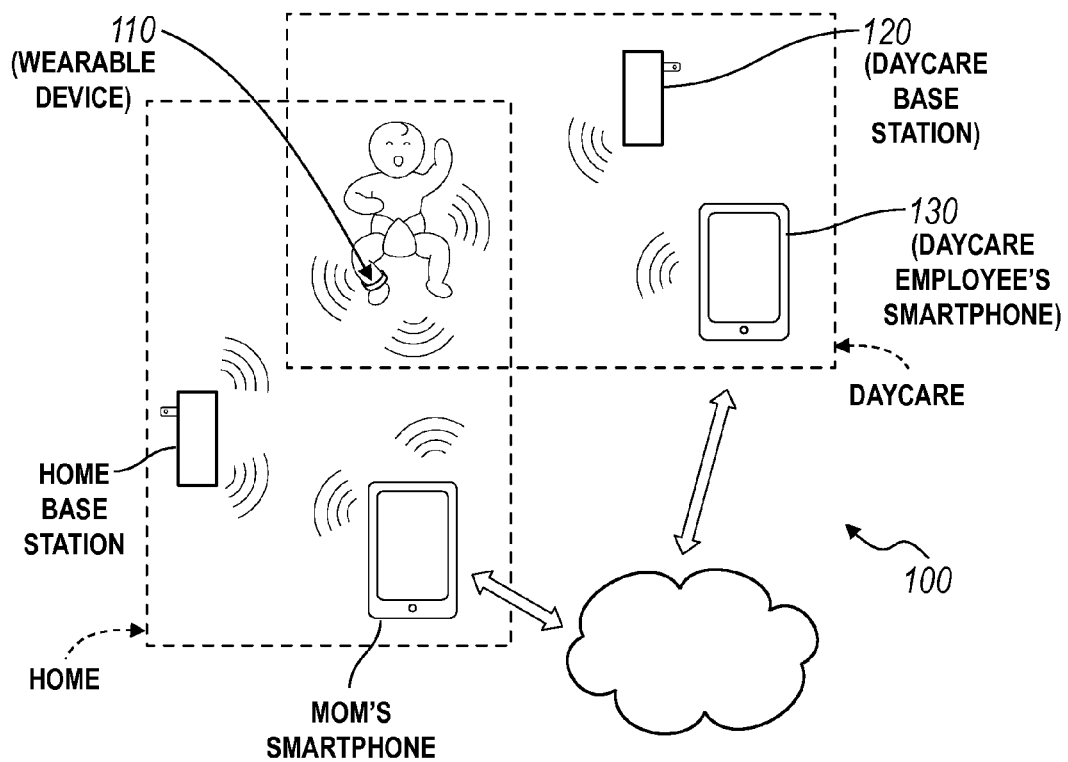
FIG. 4 is a flowchart representation of one variation of the system.

As shown in FIG. 4, multiple base stations and mobile computing devices can therefore function as a mesh network to collect ambient data and infant vitals data from the wearable device over time and to upload or transmit these data to a particular base device, mobile computing device, infant account, and/or application server, etc., thereby enabling substantially seamless monitoring of the infant across a variety of locations and with various individuals performing as parent or guardian of the infant over time.

Figure 5:
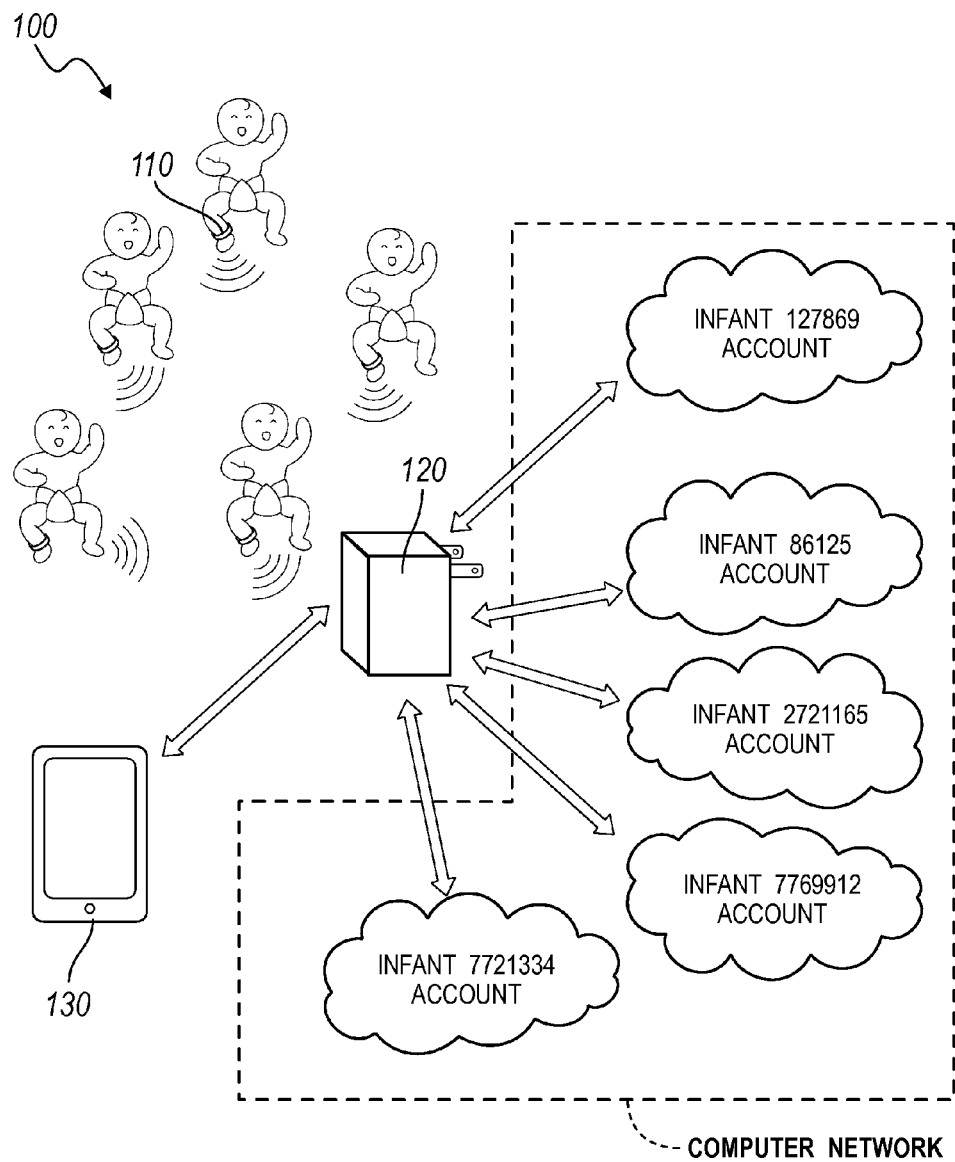
FIG. 5 is a flowchart representation of one variation of the system.

A single base station or a single mobile computing device can also function to collect infant vitals data from multiple wearable devices, each corresponding to a unique infant, and the system can merge the infant vitals data collected by each wearable device with locally-collected ambient data and store these data is corresponding accounts of the multiple infants within the application server. For example, as shown in FIG. 5, a single base station can be located within a daycare facility that accommodates multiple infants, and the base station can collect infant vitals data from a wearable device (e.g., according to a corresponding unique ID) worn by each infant at the daycare facility and upload these data with local ambient data to corresponding accounts of the various infants. Furthermore, in this example, when a problem or noteworthy issue corresponding to a particular infant at the daycare is identified, the application server can push an infant-specific alert or notification to an employee of the daycare facility to prompt fulfillment of a special need determined for the particular infant. In another example, a single base station can be arranged within a home with multiple infants, and the base station and one or more mobile computing devices of family members (e.g., parents) of the infant can cooperate to collect ambient and infant vitals data for each of the infants and to upload these data to corresponding discrete infant accounts within the application server. The application server can then manipulate these data to generate infant-specific alerts and notifications and to push these alerts and notifications back to the mobile computing device(s) within the home. In this example, a single instance of the native infant monitoring application executing on a mobile computing device of a parent of the multiple infants within the home can further support access to data for each of the infants linked to the instance of the native infant monitoring application.

However, the system can include any other number of wearable devices, base stations, user interfaces and native infant monitoring application executing on various mobile computing devices, application servers, etc. to enable collection of ambient condition data and infant vitals data for one or more infants and generation of infant-specific alerts, notifications, and predictions over time.

The systems and methods of the invention can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of an infant computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A computer implemented method for monitoring sleep of a user, comprising:
   at a computing system, linking a wearable device to an account assigned to the user;
   at the computing system, linking a mobile computing device to the account assigned to the user;
   at the computing system, assigning a collective wakefulness model to the user for a first time period, the collective wakefulness model generated from sleep data collected from a set of other users;
   at the wearable device worn by the user, collecting a first set of vitals data during the first time period;
   at the wearable device worn by the user, transmitting the first set of vitals data to the computing system;
   at the computing system, storing the first set of vitals data collected by the wearable device worn by the user during the first time period;

at the computing system, extrapolating, from the collective wakefulness model, a first waking time of the user for a first sleep event during first time period based on data in the first set of vitals data;

at the computing system, prior to the first waking time, queuing the first waking time for transmission to the mobile computing device linked to the account for presentation to a guardian of the user;

at the computing system, in response to expiration of the first time period, generating an individual wakefulness model specific to the user based on the first set of vitals data collected during the first time period;

at the computing system, assigning the individual wakefulness model to the user for a second time period succeeding the first time period;

at the computing system, extrapolating, from the individual wakefulness model, a second waking time of the user for a second sleep event during the second time period based on a second set of vitals data received from the wearable device during the second time period; and at the computing system, prior to the second waking time, queuing the second waking time for transmission to the mobile computing device for presentation to the guardian.

2. The method of claim 1, wherein assigning the collective wakefulness model to the user for the first time period comprises selecting a default collective wakefulness model for the user for the first time coinciding with a first use of the wearable device by the user.

3. The method of claim 2, wherein selecting the default collective wakefulness model for the user comprises retrieving an age of the user, correlating the age of the user with a particular development stage of the user, and selecting a default collective wakefulness model generated from sleep data collected from other users during the particular development stage.

4. The method of claim 1, wherein generating the individual wakefulness model comprises generating the individual wakefulness model specific to the user based on the first set of vitals data collected by the wearable device worn by the user and exclusive of vitals data collected from other users.

5. The method of claim 1, wherein generating the individual wakefulness model specific to the user comprises training a new wakefulness model specific to the user based on the first set of vitals data collected during the first time period and based on wakefulness states of the user during sleep events in the first time period determined from wakefulness states of other users in the set of other users.

6. The method of claim 1,
wherein assigning the collective wakefulness model for the user for the first time period comprises assigning a default collective wakefulness model to the user for a first development stage of the user;
wherein generating the individual wakefulness model comprises, in response to expiration of the first development stage, generating the individual wakefulness model based on the first set of vitals data received from the wearable device during the first development stage and assigning the individual wakefulness model to the user a duration of a second development stage of the user succeeding the first development stage; and
further comprising, in response to expiration of the second development stage, generating a second individual wakefulness model specific to the user based on a third set of vitals data received from the wearable device during the second development stage and assigning the second individual wakefulness model to the user for a duration of a third development stage of the user succeeding the second development stage.

7. The method of claim 6, further comprising extracting a development trend of the user from the second set of vitals data and the third set of vitals data and predicting a date of a future development event of the user based on a comparison of the development trend to a development history of an other user, the future development event selected from the group comprising: a teething event, a rollover event, a crawling event, a walking event, and a first word event.

8. The method of claim 1, further comprising extrapolating, from the individual wakefulness model, a revised second waking time of the user for the second sleep event based on a third set of vitals data received from the wearable device succeeding receipt of the second set of vitals data during the second time period.

9. The method of claim 8, wherein extrapolating the second predicted waking time of the user comprises extrapolating the second predicted waking time within a first confidence band; and wherein extrapolating the revised second predicted waking time of the user comprises extrapolating the revised second predicted waking time within a second confidence ban narrow than the first confidence band.

10. The method of claim 1,
wherein collecting the first set of vitals data during the first time period comprises collecting a time series of heart rate data, a time series of skin temperature data, and a time series of motion data; and
wherein the method further comprises:
linking a base station to the account;
routing the first set of vitals data through the linked base station;
at the base station, collecting a first set of ambient condition data comprising a time series of ambient temperature data, a time series of ambient noise data, a time series of ambient light data, and a time series of ambient humidity data;
combining the first set of vitals data and the first set of ambient condition data;
at the base station, transmitting the combined first set of vitals data and first set of ambient condition data to the computing system; and
wherein extrapolating the first predicted waking time of the user comprises extrapolating the first predicted waking time of the user for the first sleep event further based on the combined first set of vitals data and first set of ambient condition data.

11. The method of claim 10, further comprising, in response to ambient noise in the time series of ambient noise data exceeding a threshold ambient noise value, transmitting an alert to the mobile computing device.

* * * * *